US007906121B2

(12) United States Patent
Chang et al.

(10) Patent No.: US 7,906,121 B2
(45) Date of Patent: Mar. 15, 2011

(54) METHODS AND COMPOSITIONS FOR GENERATING BIOACTIVE ASSEMBLIES OF INCREASED COMPLEXITY AND USES

(75) Inventors: Chien-Hsing Chang, Downingtown, PA (US); David M. Goldenberg, Mendham, NJ (US); William J. McBride, Boonton, NJ (US); Edmund A. Rossi, Woodland Park, NJ (US)

(73) Assignee: IBC Pharmaceuticals, Inc., Morris Plains, NJ (US)

( * ) Notice: Subject to any disclaimer, the term of this patent is extended or adjusted under 35 U.S.C. 154(b) by 0 days.

(21) Appl. No.: 12/417,917

(22) Filed: Apr. 3, 2009

(65) Prior Publication Data

US 2009/0202433 A1 Aug. 13, 2009

Related U.S. Application Data

(60) Division of application No. 11/478,021, filed on Jun. 29, 2006, now Pat. No. 7,534,866, which is a continuation-in-part of application No. PCT/US2006/010762, filed on Mar. 24, 2006, and a continuation-in-part of application No. PCT/US2006/012084, filed on Mar. 29, 2006, and a continuation-in-part of application No. 11/389,358, filed on Mar. 24, 2006, now Pat. No. 7,550,143, and a continuation-in-part of application No. 11/391,584, filed on Mar. 28, 2006, now Pat. No. 7,521,056.

(60) Provisional application No. 60/728,292, filed on Oct. 19, 2005, provisional application No. 60/751,196, filed on Dec. 16, 2005, provisional application No. 60/782,332, filed on Mar. 14, 2006.

(51) Int. Cl.
*A61K 39/44* (2006.01)
*A61K 38/19* (2006.01)
*A61K 38/38* (2006.01)
*A61K 38/21* (2006.01)
*A61K 38/17* (2006.01)
*A61K 39/385* (2006.01)
*A61K 51/12* (2006.01)
*A61K 49/00* (2006.01)

(52) U.S. Cl. .......... 424/178.1; 424/185.1; 424/192.1; 424/193.1; 424/85.1; 424/85.2; 424/85.5; 424/130.1; 424/134.1; 424/135.1; 424/136.1; 424/9.321; 424/1.41; 424/1.49; 424/1.65; 514/7.7; 514/21.3

(58) Field of Classification Search .......... None
See application file for complete search history.

(56) References Cited

U.S. PATENT DOCUMENTS

| 4,046,722 A | 9/1977 | Rowland |
| 4,699,784 A | 10/1987 | Shih et al. |
| 4,868,109 A | 9/1989 | Lansdorp et al. |
| 6,306,393 B1 | 10/2001 | Goldenberg |
| 6,524,854 B1 | 2/2003 | Monia et al. |
| 7,060,506 B2 | 6/2006 | Craig |
| 7,521,056 B2 | 4/2009 | Chang et al. |
| 7,527,787 B2 * | 5/2009 | Chang et al. ............... 424/133.1 |
| 7,534,866 B2 * | 5/2009 | Chang et al. ............... 530/350 |
| 7,550,143 B2 | 6/2009 | Chang et al. |
| 7,666,400 B2 * | 2/2010 | Chang et al. ............... 424/85.1 |
| 2003/0198956 A1 | 10/2003 | Makowski et al. |
| 2003/0219433 A1 | 11/2003 | Hansen et al. |
| 2003/0232420 A1 | 12/2003 | Braun et al. |
| 2004/0018587 A1 | 1/2004 | Makowski et al. |
| 2005/0003403 A1 | 1/2005 | Rossi et al. |
| 2006/0228300 A1 * | 10/2006 | Chang et al. ............... 424/1.49 |
| 2006/0228357 A1 * | 10/2006 | Chang et al. ............... 424/144.1 |
| 2007/0086942 A1 * | 4/2007 | Chang et al. ............... 424/1.49 |
| 2007/0140966 A1 * | 6/2007 | Chang et al. ............... 424/1.49 |
| 2007/0264265 A1 | 11/2007 | Goldenberg et al. |
| 2008/0171067 A1 * | 7/2008 | Govindan et al. ............ 424/280.1 |
| 2009/0060862 A1 * | 3/2009 | Chang et al. ............... 424/85.2 |
| 2009/0191225 A1 * | 7/2009 | Chang et al. ............... 424/181.1 |
| 2009/0202487 A1 * | 8/2009 | Chang et al. ............... 424/85.7 |
| 2009/0269277 A1 * | 10/2009 | Chang et al. ............... 424/1.49 |
| 2010/0068137 A1 * | 3/2010 | Chang et al. ............... 424/1.49 |
| 2010/0189641 A1 * | 7/2010 | Chang et al. ............... 424/1.11 |
| 2010/0189689 A1 * | 7/2010 | Chang et al. ............... 424/85.7 |
| 2010/0221210 A1 * | 9/2010 | Chang et al. ............... 424/85.2 |
| 2010/0261885 A1 * | 10/2010 | Chang et al. ............... 530/351 |

FOREIGN PATENT DOCUMENTS

| WO | 0068248 | 11/2000 |
| WO | 2006/107617 | 10/2006 |
| WO | 2006/107786 | 10/2006 |
| WO | 2007075270 | 7/2007 |

OTHER PUBLICATIONS

Alto et al. "Bioinformatic design of A-kinase anchoring protein-in silico: a potent and selective peptide antagonist of type II protein kinase A anchoring" Proc. Natl. Acad. Sci USA Apr. 15, 2003; 100(8):4445-50.

Banky et al. "Dimerization/Docking Domain of the Type Iα Regulatory Subunit of cAMP-dependent Protein Kinase", J. Biol. Chem. 273:35048-55, 1998.

Carr et al. "Interaction of the Regulatory Subunit (RII) of cAMP-dependent Protein Kinase with RII-anchoring Proteins Occurs through an Amphipathic Helix Binding Motif", J. Biol. Chem. 266:14188-92 (1991).

(Continued)

*Primary Examiner* — Phuong Huynh
(74) *Attorney, Agent, or Firm* — Richard A. Nakashima

(57) ABSTRACT

The present invention concerns methods and compositions for making and using bioactive assemblies of defined compositions, which may have multiple functionalities and/or binding specificities. In particular embodiments, the bioactive assembly is formed using dock-and-lock (DNL) methodology, which takes advantage of the specific binding interaction between dimerization and docking domains (DDD) and anchoring domains (AD) to form the assembly. In various embodiments, one or more effectors may be attached to a DDD or AD sequence. Complementary AD or DDD sequences may be attached to an adaptor module that forms the core of the bioactive assembly, allowing formation of the assembly through the specific DDD/AD binding interactions. Such assemblies may be attached to a wide variety of effector moieties for treatment, detection and/or diagnosis of a disease, pathogen infection or other medical or veterinary condition.

25 Claims, 6 Drawing Sheets

OTHER PUBLICATIONS

Colledge et al. "AKAPs: from structure to function", Trends Cell Biol. 6:216-21 (1999).

Corbin et al. "Regulation of Adenosine 3',5'-Monophosphate-dependent Protein Kinase", J. Biol. Chem. 248:1813-21 (1973).

Dodart et al. "Immunotherapy for Alzheimer's Disease: will vaccination work?" Trends Mol. Med. 9(3):85-87 (2003).

Gillies et al. "High-level expression of chimeric antibodies using adapted cDNA variable region cassettes", J. Immunol. Methods 125 (1989) 191-202.

Gold et al. "A Novel Bispecific, Trivalent Antibody Construct for Targeting Pancreatic Carcinoma", Cancer Res. 68:4819-26, 2008.

Goldenberg et al. "Multifunctional Antibodies by the Dock-and-Lock Method for Improved Cancer Imaging and Therapy by Pretargeting", J. Nucl. Med. 49:158-63, 2008.

Hausken et al. "Mutational Analysis of the A-Kinase Anchoring Protein (AKAP)-binding Site on RII", J. Biol. Chem. 271:29016-22 (1996).

Hodneland et al. "Selective immobilization of proteins to self-assembled monolayers presenting active site-directed capture ligands", Proc. Natl. Acd. Sci. USA 2002; 99:5048-5052.

Lohmann et al. "High-affinity binding of the regulatory subunit (RII) of cAMP-dependent protein kinase to microtubule-associated and other cellular proteins", Proc. Natl. Acad. Sci. USA 81:6723-27 (1984).

Mason, Anthony J. "Functional Analysis of the Cysteine Residues of Activin A", Mol. Endocrinol. 8:325-32, 1994.

Newlon et al. "A Novel Mechanism of PKA Anchoring Revealed by Solution Structures of Anchoring Complexes", EMBO J. 2001; 20:1651-1662.

Newlon et al. "The molecular basis for protein kinase A anchoring revealed by solution NMR", Nature Struct. Biol. 1999; 3:222-227.

Ngo et al. "Computational Complexity, Protein Structure Prediction, and the Levinthal Paradox", The Protein Folding Problem and Tertiary Structure Prediction, Ch. 14, pp. 492-495, (Mertz & Le Grand, Eds.), Birkhauser Boston, 1994.

Oyen et al. "Human testis cDNA for the regulatory subunit RIIα of cAMP-dependent protein kinase encodes an alternate amino-terminal region", FEBS Letters 246:57-64, 1989.

Rabjohn et al. "Molecular Cloning and Epitope Analysis of the Peanut Allergen Ara h 3" J. Clinical Investigation 103 (4):535-542 (1999).

Rose et al. "Structural basis of dimerization, coactivator recognition and MODY3 mutations in HNF-1α", Nature Struct. Biol. 2000; 7:744-748.

Rossi et al. "Novel Designs of Multivalent Anti-CD20 Humanized Antibodies as Improved Lymphoma Therapeutics", Cancer Res. 68:8384-92, 2008.

Rustandi et al. "The Ca2+-Dependent Interaction of S100B(ββ) with a Peptide Derived from p53", Biochemistry 1998; 37: 1951-1960.

Scott et al. "Type II Regulatory Subunit Dimerization Determines the Subcellular Localization of the cAMP-dependent Protein Kinase", J. Biol. Chem. 265:21561-66 (1990).

Seffernick et al. "Melamine Deaminase and Atrazine Chlorohydrolase: 98 Percent Identical but Functionally Different" J. Bacteriol. 183(8):2405-2410 (2001).

Sharkey et al. "Improved Therapeutic Results by Pretargeted Radioimmunotherapy of Non-Hodgkin's Lymphoma with a New Recombinant, Trivalent, Anti-CD20, Bispecific Antibody", Cancer Res. 68:5282-90, 2008.

Sharkey et al. "Metastatic Human Colonic Carcinoma: Molecular Imaging with Pretargeted SPECT and PET in a Mouse Model", Radiology 246:497-507, 2008.

Stryer et al. "Levels of Structure in Protein Architecture", Biochemistry, 3rd Ed., pp. 31-33, W.H. Freeman & Co., New York, 1998.

Winkler et al. "Changing the Antigen Binding Specificity by Single Point Mutations of an Anti-p24 (HIV-1) Antibody", J. Immunol. 165:4505-14, 2000.

Witkowski et al. "Conversion of a β-Ketoacyl Synthase to a Malonyl Decarboxylase by Replacement of the Active-Site Cysteine with Glutamine" Biochemistry 38(36):11643-50 (1999).

Wong et al. "AKAP Signalling Complexes: Focal Points in Space and Time", Nat. Rev. Mol. Cell Biol. 12:959-70 (2004).

Zhu et al. "Inhibition of tumor growth and metastasis by targeting tumor-associated angiogenesis with antagonists to the receptors of vascular endothelial growth factor", Invest. New Drugs 17:195-212, 1999.

Abbas et al. Cellular and Molecular Immunology, W.B. Saunders Comp. 1991, p. 43.

Backer et al. "Self-Assembled "Dock and Lock" System for Linking Payloads to Targeting Proteins" Bioconjugate Chem., 2006, 17(4):912-919.

Baillie et al. "Compartmentalisation of phospodiesterases and protein kinase A: opposites attract", FEBS Letters 2005; 579:3264-3270.

Basu et al. "Structure-Function Engineering of Interferon-β-1b for Improving Stability, Solubility, Potency, Immunogenicity, and Pharmacokinetic Properties by Site-Selective Mono-PEGylation", Bioconjugate Chem. 2006; 17:618-630.

Burns-Hamuro et al. "Distinct interaction modes of an AKAP bound to two regulatory subunit isoforms of protein kinase A revealed by amide hydrogen/deuterium exchange" Protein Science (2005), 14:2982-2992.

Carr et al. "Identification of Sperm-specific Proteins That Interact with A-kinase Anchoring Proteins in a Manner Similar to the Type II Regulatory Subunit of PKA" J. Biol. Chem. 276(20):17332-17338 (2001).

Chang et al. "The Dock and Lock Method: A Novel Platform Technology for Building Multivalent, Multifunctional Structures of Defined Composition with Retained Bioactivity" Clin. Cancer Res. Sep. 15, 2007;13(18 Suppl), pp. 5586-5591.

Dhalluin et al."Structural and Biophysical Characterization of the 40 kDa PEG-Interferon-α2a and Its Individual Positional Isomers" Bioconjugate Chem. 2005;16:504-517.

Doherty et al. "Site-Specific PEGylation of Engineered Cysteine Analogues of Recombinant Human Granulocyte-Macrophage Colony-Stimulating Factor", Bioconjugate Chem. 2005;16:1291-1298.

Gold et al. "Molecular Basis of AKAP Specificity for PKA Regulatory Subunits" Mol. Cell Nov. 3, 2006;24(3):383-95.

Goodson and Katre "Site-Directed PEGylation of Recombinant Interleukin-2 at its Glycosylation Site", Nat. Biotechnology Apr. 1990;8(4):343-6.

Grace et al. "Site of Pegylation and Polyethylene Glycol Molecule Size Attenuate Interferon-α Antiviral and Antiproliferative Activities through the JAK/STAT Signaling Pathway" J. Biol. Chem. 2005;280(8):6327-6336.

Hundsrucker et al. "High-affinity AKAP7σ-protein kinase A interaction yields novel protein kinase A-anchoring disruptor peptides" Biochem. J. (2006) 396, 297-306.

Kinderman et al. "A Novel and Dynamic Mechanism for AKAP Binding to RII Isoforms of cAMP-dependent Protein Kinase" Mol. Cell 24(3):397-408 (2006).

Kinstler et al. "Characterization and Stability of N-terminally PEGylated rhG-CSF" Pharm. Res. 1996;13(7):996-1002.

Lee et al. "Solid-Phase PEGylation of Recombinant Interferon α-2a for Site-Specific Modification: Process Performance, Characterization, and in Vitro Bioactivity" Bioconjugate Chem. 2007; 18:1728-34.

Pepinsky et al. "Improved Pharmacokinetic Properties of a Polyethylene Glycol-Modified Form of Interferon-β-1a with Preserved in Vitro Bioactivity" Pharmacol. Exp. Ther. 2001; 297(3):1059-1066.

Rosendahl et al. "A Long-Acting, Highly Potent Interferon α-2 Conjugate Created Using Site-Specific PEGylation" Bioconjugate Chem. 2005;16:200-207.

Rossi et al. "Stably tethered multifunctional structures of defined composition made by the dock and lock method for use in cancer targeting" Proc. Natl. Acad. Sci. Epub Apr. 24, 2006, vol. 103, No. 18, pp. 6841-6846.

Stokka et al. "Characterization of A-kinase-anchoring disruption using a solution-based assay" Biochem. J. (2006) 400, 493-499.

* cited by examiner

Figure 1

A. DDD2:
CGHIQIPPGLTELLQGYTVEVLRQQ
PPDLVEFAVEYFTRLREARA (SEQ ID NO:1)

B. AD2:
CGQIEYLAKQIVDNAIQQAGC (SEQ ID NO:2)

C. DDD3:
SLRECELYVQKHNIQALLKDSIVQLCTARPERPMAFLREYFERLEKEE
AK (SEQ ID NO:3)

D. DDD3C
MSCGGSLRECELYVQKHNIQALLKDSIVQLCTARPERPMAFLREYFE
RLEKEEAK (SEQ ID NO:4)

E. AD3
CGFEELAWKIAKMIWSDVFQQGC (SEQ ID NO:5)

Type-d adaptor module

Figure 6

Complete amino acid sequence of DDD3C-CH2-CH3-AD2

DD3C — MS C GGSLRECELYVQKHNIQALLKDSIVQLCTARPERPMAFLREYFERLEKEEAK (SEQ ID NO:4)

Link-1 — GRSG (SEQ ID NO:6)

CH2 — APELLGGPSVFLFPPKPKDTLMISRTPEVTCVVVDVSHEDPEVKFNWYVDGVEV HNAKTKPREEQYNSTYRVVSVLTVLHQDWLNGKEYKCKVSNKALPAPIEKTISKAK (SEQ ID NO:7)

CH3 — GQPREPQVYTLPPSREEMTKNQVSLTCLVKGFYPSDIAVEWESNGQPENNYKT TPPVLDSDGSFFLYSKLTVDKSRWQQGNVFSCSVMHEALHNHYTQKSLSLSPGK (SEQ ID NO:8)

Link-2 — GSGGGGSGG (SEQ ID NO:9)

AD2 — CGQIEYLAKQIVDNAIQQAG C (SEQ ID NO:2)

METHODS AND COMPOSITIONS FOR GENERATING BIOACTIVE ASSEMBLIES OF INCREASED COMPLEXITY AND USES

RELATED APPLICATIONS

The present application is a divisional of U.S. patent application Ser. No. 11/478,021, filed Jun. 29, 2006, now U.S. Pat. No. 7,534,866 which is a continuation-in-part of PCT Application Serial Nos. PCT/US2006/010762, filed Mar. 24, 2006, and PCT/US2006/012084, filed Mar. 29, 2006; and a continuation-in-part of U.S. patent application Ser. Nos. 11/389,358, filed Mar. 24, 2006, which is now U.S. Pat. No. 7,550,143 and 11/391,584, filed Mar. 28, 2006, which is now U.S. Pat. No. 7,521,056; and claims the benefit under 35 U.S.C. §119(e) of provisional U.S. patent application Ser. Nos. 60/728,292, filed Oct. 19, 2005; 60/751,196, filed Dec. 16, 2005; and 60/782,332, filed Mar. 14, 2006, each cited application incorporated herein by reference in its entirety.

FIELD OF THE INVENTION

Various embodiments of the present invention concern methods and compositions for making and using multivalent, multispecific and/or multifunctional complexes. Such complexes find use in a wide variety of applications, particularly in the field of treatment, detection and/or diagnosis of infections, diseases and other health-related conditions, including but not limited to cancer, autoimmune disease, cardiovascular disease, metabolic diseases, degenerative diseases, including such neurologic disorders as Alzheimer's, and organ transplant rejection.

BACKGROUND OF THE INVENTION

Man-made agents that incorporate multiple copies of both targeting and effector moieties are highly desirable, as they should provide more avid binding and confer enhanced potency. Although recombinant technologies are commonly applied for making fusion proteins with both targeting and effector domains, multimeric structures that comprise the same or different monomeric components to acquire multivalency or multifunctionality may be obtained only with judicious applications of conjugation chemistries.

For agents generated by recombinant engineering, problems may include high manufacturing cost, low expression yields, instability in serum, instability in solution resulting in formation of aggregates or dissociated subunits, undefined batch composition due to the presence of multiple product forms, contaminating side-products, reduced functional activities or binding affinity/avidity attributed to steric factors or altered conformations, etc. For agents generated by various methods of chemical cross-linking, high manufacturing cost and heterogeneity of the purified product are two major limitations.

Thus, there remains a need in the art for a general method of making multivalent structures of multiple specificities or functionalities, which are of defined composition, homogeneous purity, and unaltered affinity, and can be produced in high yields without the requirement of extensive purification. Furthermore, such structures must also be sufficiently stable in serum to allow in vivo applications. A need also exists for stable, multivalent structures of multiple specificities or functionalities that are easy to construct and/or obtain in relatively purified form.

SUMMARY

The present invention discloses a platform technology for generating bioactive assemblies of increased complexity that are suitable for in vitro as well as in vivo applications. The assemblies are built by site-specific conjugation of at least two different proteins or nonproteins using a strategy that is based on the Dock and Lock (DNL) method as discussed in U.S. provisional patent applications 60/728,292, filed Oct. 19, 2005; 60/751,196, filed Dec. 16, 2005; 60/782,332, filed Mar. 14, 2006; and U.S. patent application Ser. Nos. 11/389, 358, filed Mar. 24, 2006 and 11/391,584, filed Mar. 28, 2006, (each of which is incorporated herein by reference in its entirety); and reported recently (Rossi et al, Proc Natl Acad Sci USA, 2006, 103: 6841-6846).

Methods of use of bioactive assemblies may include detection, diagnosis and/or treatment of a disease or other medical condition. Such conditions may include, but are not limited to, cancer, hyperplasia, diabetic retinopathy, macular degeneration, inflammatory bowel disease, Crohn's disease, ulcerative colitis, rheumatoid arthritis, diabetes, sarcoidosis, asthma, edema, pulmonary hypertension, psoriasis, corneal graft rejection, neovascular glaucoma, Osler-Webber Syndrome, myocardial angiogenesis, plaque neovascularization, restenosis, neointima formation after vascular trauma, telangiectasia, hemophiliac joints, angiofibroma, fibrosis associated with chronic inflammation, lung fibrosis, amyloidosis, Alzheimer's disease, organ transplant rejection, deep venous thrombosis or wound granulation.

In particular embodiments, the disclosed methods and compositions may be of use to treat autoimmune disease, such as acute idiopathic thrombocytopenic purpura, chronic idiopathic thrombocytopenic purpura, dermatomyositis, Sydenham's chorea, myasthenia gravis, systemic lupus erythematosus, lupus nephritis, rheumatic fever, polyglandular syndromes, bullous pemphigoid, juvenile diabetes mellitus, Henoch-Schonlein purpura, post-streptococcal nephritis, erythema nodosum, Takayasu's arteritis, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitisubiterans, Sjogren's syndrome, primary biliary cirrhosis, Hashimoto's thyroiditis, thyrotoxicosis (i.e., Graves' disease), scleroderma, chronic active hepatitis, polymyositis/dermatomyositis, polychondritis, pemphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis, psoriasis or fibrosing alveolitis.

In certain embodiments, the bioactive assemblies may be of use for therapeutic treatment of cancer. It is anticipated that any type of tumor and any type of tumor antigen may be targeted. Exemplary types of tumors that may be targeted include acute lymphocytic leukemia, acute myelogenous leukemia, biliary cancer, breast cancer, cervical cancer, chronic lymphocytic leukemia, chronic myelogenous leukemia, colorectal cancer, endometrial cancer, esophageal cancer, gastric cancer, head and neck cancers, Hodgkin's lymphoma, lung cancer, medullary thyroid cancer, non-Hodgkin's lymphoma, multiple myeloma, renal cancer, ovarian cancer, pancreatic cancer, melanoma, liver cancer, prostate cancer, glial and other brain and spinal cord tumors, and urinary bladder cancer.

Tumor-associated antigens that may be targeted include, but are not limited to, carbonic anhydrase IX, A3, antigen specific for A33 antibody, BrE3-antigen, CD1, CD1a, CD3, CD5, CD15, CD16, CD19, CD20, CD21, CD22, CD23, CD25, CD30, CD45, CD74, CD79a, CD80, HLA-DR, NCA 95, NCA90, HCG and its subunits, CEA (CEACAM-5), CEACAM-6, CSAp, EGFR, EGP-1, EGP-2, Ep-CAM, Ba 733, HER2/neu, hypoxia inducible factor (HIF), KC4-antigen, KS-1-antigen, KS1-4, Le-Y, macrophage inhibition factor (MIF), MAGE, MUC 1, MUC2, MUC3, MUC4, MUC16, PAM-4-antigen, PSA, PSMA, RS5, S100, TAG-72, p53, tenascin, IL-6, IL-8, insulin growth factor-1 (IGF-1), Tn antigen, Thomson-Friedenreich antigens, tumor necrosis antigens, VEGF, placenta growth factor (P1GF), 17-1A-antigen, an angiogenesis marker (e.g., ED-B fibronectin), an oncogene marker (e.g., bcl-2), an oncogene product, and other tumor-associated antigens. Recent reports on tumor associated antigens include Mizukami et al., (2005, *Nature Med.* 11:992-97); Hatfield et al., (2005, *Curr. Cancer Drug Targets* 5:229-48); Vallbohmer et al. (2005, *J. Clin. Oncol.* 23:3536-44); and Ren et al. (2005, *Ann. Surg.* 242:55-63), each incorporated herein by reference.

In other embodiments, the bioactive assemblies may be of use to treat infection with pathogenic organisms, such as bacteria, viruses, fungi, or unicellular parasites. Exemplary fungi that may be treated include *Microsporum, Trichophyton, Epidermophyton, Sporothrix schenckii, Cryptococcus neoformans, Coccidioides immitis, Histoplasma capsulatum, Blastomyces dermatitidis* or *Candida albican.* Exemplary viruses include human immunodeficiency virus (HIV), herpes virus, cytomegalovirus, rabies virus, influenza virus, human papilloma virus, hepatitis B virus, hepatitis C virus, Sendai virus, feline leukemia virus, Reo virus, polio virus, human serum parvo-like virus, simian virus 40, respiratory syncytial virus, mouse mammary tumor virus, Varicella-Zoster virus, Dengue virus, rubella virus, measles virus, adenovirus, human T-cell leukemia viruses, Epstein-Barr virus, murine leukemia virus, mumps virus, vesicular stomatitis virus, Sindbis virus, lymphocytic choriomeningitis virus or blue tongue virus. Exemplary bacteria include *Bacillus anthracis, Streptococcus agalactiae, Legionella pneumophilia, Streptococcus pyogenes, Escherichia coli, Neisseria gonorrhoeae, Neisseria meningitidis, Pneumococcus* spp., *Hemophilis influenzae* B, *Treponema pallidum,* Lyme disease spirochetes, *Pseudomonas aeruginosa, Mycobacterium leprae, Brucella abortus, Mycobacterium tuberculosis* or a *Mycoplasma.* Exemplary parasites include *Giardia lamblia, Giardia* spp., *Pneumocystis carinii, Toxoplasma gondii, Cryptospordium* spp., *Acanthamoeba* spp., *Naegleria* spp., *Leishmania* spp., *Balantidium coli, Trypanosoma evansi, Trypanosoma* spp., *Dientamoeba fragilis, Trichomonas vaginalis, Trichmonas* spp. *Entamoeba* spp. *Dientamoeba* spp. *Babesia* spp., *Plasmodium falciparum, Isospora* spp., *Toxoplasma* spp. *Enterocytozoon* spp., *Pneumocystis* spp. and *Balantidium* spp.

Although not limiting, in various embodiments, one or more protein or peptide therapeutic or diagnostic agents may be attached to or incorporated into a bioactive assembly, such as a bacterial toxin, a plant toxin, ricin, abrin, a ribonuclease (RNase), DNase I, Staphylococcal enterotoxin-A, pokeweed antiviral protein, gelonin, diphtherin toxin, *Pseudomonas* exotoxin, *Pseudomonas* endotoxin, Ranpirnase (Rap), Rap (N69Q), PE38, dgA, DT390, PLC, tPA, a cytokine, a growth factor, a soluble receptor component, surfactant protein D, IL-4, sIL-4R, sIL-13R, $VEGF_{121}$, TPO, EPO, a clot-dissolving agent, an enzyme, a fluorescent protein, $sTNF\alpha$-R, an avimer, a scFv, a dsFv or a nanobody.

In other embodiments, an anti-angiogenic agent may form part of or may be attached to a bioactive assembly. Exemplary anti-angiogenic agents of use include angiostatin, baculostatin, canstatin, maspin, anti-VEGF antibodies or peptides, anti-placental growth factor antibodies or peptides, anti-Flk-1 antibodies, anti-Flt-1 antibodies or peptides, laminin peptides, fibronectin peptides, plasminogen activator inhibitors, tissue metalloproteinase inhibitors, interferons, interleukin 12, IP-10, Gro-β, thrombospondin, 2-methoxyoestradiol, proliferin-related protein, carboxiamidotriazole, CM101, Marimastat, pentosan polysulphate, angiopoietin 2, interferon-alpha, herbimycin A, PNU145156E, 16K prolactin fragment, Linomide, thalidomide, pentoxifylline, genistein, TNP-470, endostatin, paclitaxel, accutin, angiostatin, cidofovir, vincristine, bleomycin, AGM-1470, platelet factor 4 or minocycline.

In still other embodiments, one or more therapeutic agents, such as aplidin, azaribine, anastrozole, azacytidine, bleomycin, bortezomib, bryostatin-1, busulfan, calicheamycin, camptothecin, 10-hydroxycamptothecin, carmustine, celebrex, chlorambucil, cisplatin, irinotecan (CPT-11), SN-38, carboplatin, cladribine, cyclophosphamide, cytarabine, dacarbazine, docetaxel, dactinomycin, daunomycin glucuronide, daunorubicin, dexamethasone, diethylstilbestrol, doxorubicin, 2-pyrrolinodoxorubicine (2P-DOX), cyano-morpholino doxorubicin, doxorubicin glucuronide, epirubicin glucuronide, ethinyl estradiol, estramustine, etoposide, etoposide glucuronide, etoposide phosphate, floxuridine (FUdR), 3',5'-O-dioleoyl-FudR (FUdR-dO), fludarabine, flutamide, fluorouracil, fluoxymesterone, gemcitabine, hydroxyprogesterone caproate, hydroxyurea, idarubicin, ifosfamide, L-asparaginase, leucovorin, lomustine, mechlorethamine, medroprogesterone acetate, megestrol acetate, melphalan, mercaptopurine, 6-mercaptopurine, methotrexate, mitoxantrone, mithramycin, mitomycin, mitotane, phenyl butyrate, prednisone, procarbazine, paclitaxel, pentostatin, PSI-341, semustine streptozocin, tamoxifen, taxanes, taxol, testosterone propionate, thalidomide, thioguanine, thiotepa, teniposide, topotecan, uracil mustard, Velcade® (bortezomib), vinblastine, vinorelbine, vincristine, ricin, abrin, ribonuclease, Onconase® (ranpirnase), rapLR1, DNase I, Staphylococcal enterotoxin-A, pokeweed antiviral protein, gelonin, diphtheria toxin, *Pseudomonas* exotoxin, *Pseudomonas* endotoxin, an antisense oligonucleotide, an interference RNA, or a combination thereof, may be conjugated to or incorporated into a bioactive assembly.

In various embodiments, one or more effectors, such as a diagnostic agent, a therapeutic agent, a chemotherapeutic agent, a radioisotope, an imaging agent, an anti-angiogenic agent, a cytokine, a chemokine, a growth factor, a drug, a prodrug, an enzyme, a binding molecule, a ligand for a cell surface receptor, a chelator, an immunomodulator, an oligonucleotide, an interference RNA, an aptamer, a hormone, a photodetectable label, a dye, a peptide, a toxin, a contrast agent, a paramagnetic label, an ultrasound label, a pro-apoptotic agent, a liposome, a nanoparticle or a combination thereof, may be attached to a bioactive assembly.

Various embodiments may concern bioactive assemblies and methods of use of same that are of use to induce apoptosis of diseased cells. Further details may be found in U.S. Patent Application Publication No. 20050079184, the entire text of which is incorporated herein by reference. Such structures may comprise a first and/or second binding moiety, such as an antibody or antibody fragment, with affinity for an antigen selected from the group consisting of CD2, CD3, CD8, CD10, CD21, CD23, CD24, CD25, CD30, CD33, CD37, CD38, CD40, CD48, CD52, CD55, CD59, CD70, CD74, CD80, CD86, CD138, CD147, HLA-DR, CEA, CSAp, CA-125, TAG-72, EFGR, HER2, HER3, HER4, IGF-1R, c-Met, PDGFR, MUC1, MUC2, MUC3, MUC4, MUC16, TNFR1, TNFR2, NGFR, Fas (CD95), DR3, DR4, DR5, DR6, VEGF, PIGF, ED-B fibronectin, tenascin, PSMA, PSA, carbonic anhydrase IX, and IL-6. In more particular embodiments, a bioactive assembly of use to induce apoptosis may comprise monoclonal antibodies, Fab fragments, chimeric, humanized or human antibodies or fragments. In preferred embodiments, the bioactive assembly may comprise combinations of anti-CD74 X anti-CD20, anti-CD74 X anti-CD22, anti-CD22 X anti-CD20, anti-CD20 X anti-HLA-DR, anti-CD19 X anti-CD20, anti-CD19 x anti-CD22, anti-CD20 X anti-CD80, anti-CD2 X anti-CD25, anti-CD8 X anti-CD25, and anti-CD2 X anti-CD147. In more preferred embodiments, the chimeric, humanized or human antibodies or antibody fragments may be derived from the variable domains of LL2 (anti-CD22), LL1 (anti-CD74) and A20 (anti-CD20).

In certain embodiments, any therapeutic protein or peptide known in the art may be attached to an AD or DDD sequence and used as an effector in the claimed methods and compositions. A large number of such therapeutic proteins or peptides are known, and are described for example, in U.S. Patent Application Publication No. 20060084794, "Albumin fusion proteins," filed Nov. 2, 2005, incorporated herein by reference in its entirety. Table 1 of 20060084794, which lists various known exemplary therapeutic proteins or peptides of use, including exemplary identifiers, patent reference numbers and preferred indications, is specifically incorporated herein by reference in its entirety. Additional therapeutic proteins or peptides of use are disclosed, for example, in U.S. Pat. No. 6,309,633, incorporated herein by reference in its entirety, and may include but are not limited to adrenocorticotropic hormone, ebiratide, angiotensin, angiotensin II, asparaginase, atrial natriuretic peptides, atrial sodium diuretic peptides, bacitracin, beta-endorphins, blood coagulation factors VII, VIII and IX, blood thymic factor, bone morphogenic factor, bone morphogenic protein, bradykinin, caerulein, calcitonin gene related polypeptide, calcitonins, CCK-8, cell growth factors, EGF, TGF-alpha, TGF-beta, acidic FGF, basic FGF, chemokines, cholecystokinin, cholecystokinin-8, cholecystokinin-pancreozymin, colistin, colony-stimulating factors, GMCSF, MCSF, corticotropin-releasing factor, cytokines, desmopressin, dipeptide, dismutase, dynorphin, eledoisin, endorphins, endothelin, endothelin-antagonistic peptides, endotherins, enkephalins, epidermal growth factor, erythropoietin, follicle-stimulating hormone, gallanin, gastric inhibitory polypeptide, gastrin-releasing polypeptide, gastrins, G-CSF, glucagon, glutathione peroxidase, glutathioperoxidase, gonadotropin, gramicidin, gramicidines, growth factor, growth hormone-releasing factor, growth hormones, h-ANP, hormone releasing hormone, human chorionic gonadotrophin, human chorionic gonadotrophin .beta.-chain, human placental lactogen, insulin, insulin-like growth factors, IGF-I, IGF-II, interferons, interleukins, intestinal polypeptide, kallikrein, kyotorphin, luliberin, luteinizing hormone, luteinizing hormone-releasing hormone, lysozyme chloride, melanocyte-stimulating hormone, melanophore stimulating hormone, mellitin, motilin, muramyl, muramyl-dipeptide, nerve growth factor, nerve nutrition factors, NT-3, NT-4, CNTF, GDNF, BDNF, neuropeptide Y, neurotensin, oxytocin, pancreastatin, pancreatic polypeptide, pancreozymin, parathyroid hormone, pentagastrin, polypeptide YY, pituitary adenyl cyclase-activating polypeptides, platelet derived growth factor, polymixin B, prolactin, protein synthesis stimulating polypeptide, PTH-related protein, relaxin, renin, secretin, serum thymic factor, somatomedins, somatostatins, substance P, superoxide, superoxide dismutase, taftsin, tetragastrin, thrombopoietin, thymic humoral factor, thymopoietin, thymosin, thymostimulin, thyroid hormone releasing hormone, thyroid-stimulating hormone, thyrotropin releasing hormone TRH, trypsin, tuftsin, tumor growth factor, tumor necrosis factor, tyrocidin, urogastrone, urokinase, vasoactive intestinal polypeptide, vasopressins, and functional equivalents.

BRIEF DESCRIPTION OF THE DRAWINGS

FIG. 1 shows exemplary peptide sequences of use in the formation of bioactive assemblies, including DDD2 (SEQ ID NO:1); AD2 (SEQ ID NO:2); DDD3 (SEQ ID NO:3); DDD3C (SEQ ID NO:4); and AD3 (SEQ ID NO:5). Compositions and methods of use of such sequences for formation of bioactive assemblies are discussed below.

FIG. 6 shows the complete amino acid sequence of an exemplary DDD3C—CH2-CH3-AD2 construct (see Example 7), comprising DDD3C (SEQ ID NO:4), a first linker (SEQ ID NO:6), CH2 (SEQ ID NO:7), CH3 (SEQ ID NO:8), a second linker (SEQ ID NO:9), and AD2 (SEQ ID NO:2).

DESCRIPTION OF ILLUSTRATIVE EMBODIMENTS

Figure 2:
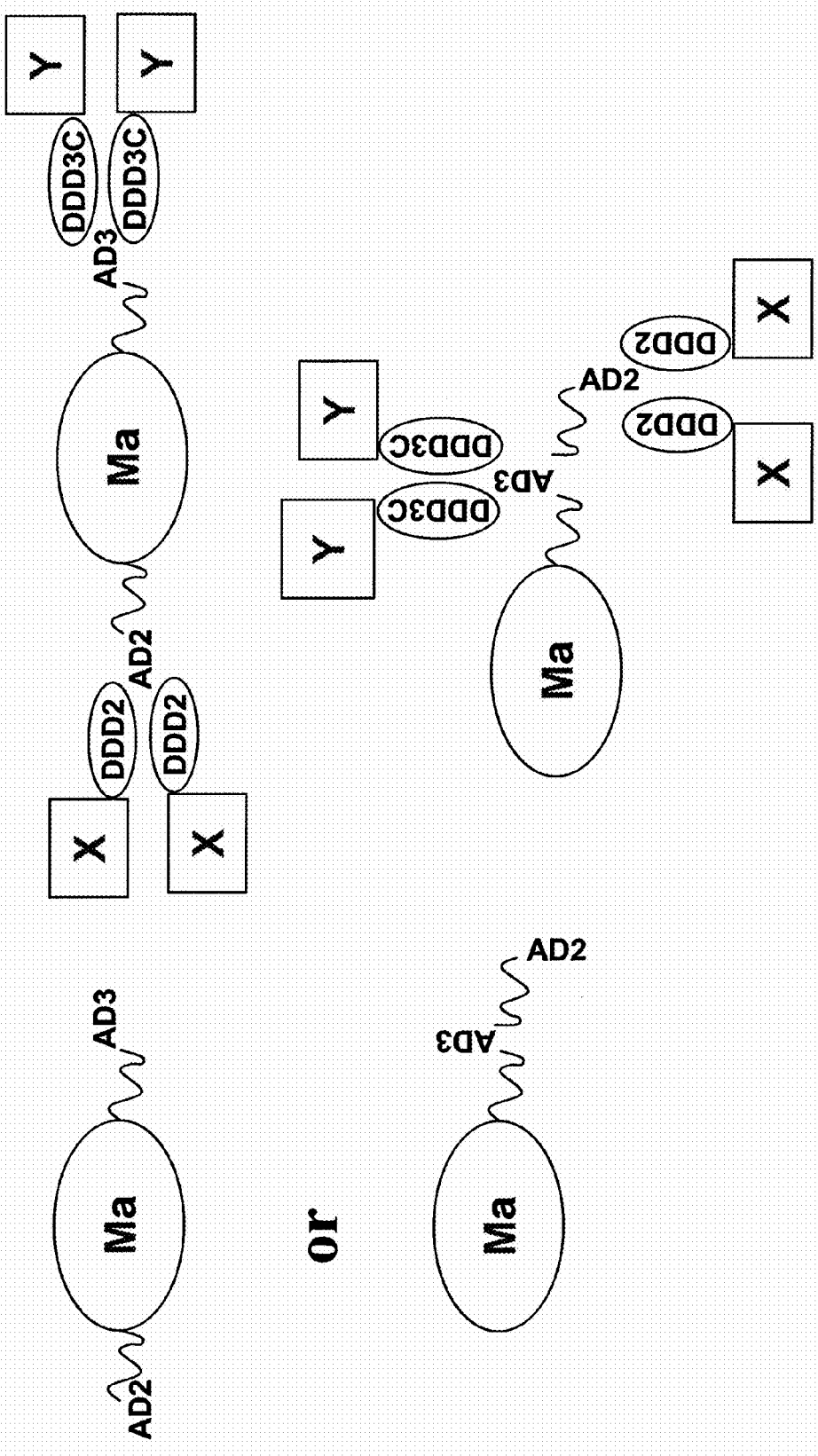
FIG. 2 shows a schematic diagram for an $X_2(Ma)Y_2$ bioactive assembly, based on a type-a adaptor molecule (Ma), for example attached to one molecule each of AD2 and AD3. The AD2 and AD3 serve as binding sites for DDD2 and DDD3C, for example. Those dimerization and docking domains may in turn be attached to a variety of effectors or binding molecules (X and Y). The result is a heterotetramer comprised of two different homodimers.

All documents, or portions of documents, cited in this application, including but not limited to patents, patent applications, articles, books, and treatises, are hereby expressly incorporated by reference in their entirety.

DEFINITIONS

As used herein, "a" or "an" may mean one or more than one of an item.

As used herein, the terms "and" and "or" may be used to mean either the conjunctive or disjunctive. That is, both terms should be understood as equivalent to "and/or" unless otherwise stated.

An antibody, as described herein, refers to a full-length (i.e., naturally occurring or formed by normal immunoglobulin gene fragment recombinatorial processes) immunoglobulin molecule (e.g., an IgG antibody) or an immunologically active (i.e., specifically binding) portion or analog of an immunoglobulin molecule, like an antibody fragment.

An antibody fragment is a portion of an antibody such as F(ab)$_2$, F(ab')$_2$, Fab, Fv, sFv and the like. Regardless of structure, an antibody fragment binds with the same antigen that is recognized by the intact antibody. The term "antibody fragment" also includes any synthetic or genetically engineered protein that acts like an antibody by binding to a specific antigen to form a complex. For example, antibody fragments include isolated fragments consisting of the variable regions, such as the "Fv" fragments consisting of the variable regions of the heavy and light chains, recombinant single chain polypeptide molecules in which light and heavy variable regions are connected by a peptide linker ("scFv proteins"), and minimal recognition units (CDR) consisting of the amino acid residues that mimic the hypervariable region.

An effector is an atom, molecule, or compound that brings about a chosen result. An effector may include a therapeutic agent and/or a diagnostic agent.

A therapeutic agent is an atom, molecule, or compound that is useful in the treatment of a disease. Examples of therapeutic agents include antibodies, antibody fragments, drugs, toxins, enzymes, nucleases, hormones, immunomodulators, antisense oligonucleotides, small interfering RNA (siRNA), aptamers, chelators, boron compounds, photoactive agents, dyes, and radioisotopes. Other exemplary therapeutic agents and methods of use are disclosed in U.S. Patent Publication Nos. 20050002945, 20040018557, 20030148409 and 20050014207, each incorporated herein by reference.

A diagnostic agent is an atom, molecule, or compound that is useful in diagnosing a disease, either by in vitro or in vivo tests. Useful diagnostic agents include, but are not limited to, radioisotopes, dyes (such as with the biotin-streptavidin complex), contrast agents, fluorescent compounds or molecules, and enhancing agents (e.g., paramagnetic ions) for magnetic resonance imaging (MRI).

An immunoconjugate is a conjugate of a binding molecule (e.g., an antibody component) with an atom, molecule, or a higher-ordered structure (e.g., with a carrier, a therapeutic agent, or a diagnostic agent).

A naked antibody is an antibody that is not conjugated to any other agent.

A carrier is an atom, molecule, or higher-ordered structure that is capable of associating with a therapeutic or diagnostic agent to facilitate delivery of such agent to a targeted cell. Carriers may include proteins, peptides, lipids (e.g., amphiphilic lipids that are capable of forming higher-ordered structures), polysaccharides (such as dextran), or other higher-ordered structures, such as micelles, liposomes, or nanoparticles.

As used herein, the term antibody fusion protein refers to a recombinantly produced antigen-binding molecule in which two or more of the same or different scFv or antibody fragments with the same or different specificities are linked. Valency of the fusion protein indicates how many binding arms or sites the fusion protein has to a single antigen or epitope; i.e., monovalent, bivalent, trivalent or multivalent. The multivalency of the antibody fusion protein means that it can take advantage of multiple interactions in binding to an antigen, thus increasing the avidity of binding to the antigen. Specificity indicates how many antigens or epitopes an antibody fusion protein is able to bind; i.e., monospecific, bispecific, trispecific, multispecific. Using these definitions, a natural antibody, e.g., an IgG, is bivalent because it has two binding arms but is monospecific because it binds to one epitope. Monospecific, multivalent fusion proteins have more than one binding site for an epitope but only binds to one such epitope, for example a diabody with two binding site reactive with the same antigen. The fusion protein may comprise a single antibody component, a multivalent or multispecific combination of different antibody components, or multiple copies of the same antibody component. The fusion protein may additionally comprise an antibody or an antibody fragment and a therapeutic agent. Examples of therapeutic agents suitable for such fusion proteins include immunomodulators ("antibody-immunomodulator fusion protein") and toxins ("antibody-toxin fusion protein"). One preferred toxin comprises a ribonuclease (RNase), preferably a recombinant RNase.

An antibody or immunoconjugate preparation, or a composition described herein, is said to be administered in a "therapeutically effective amount" if the amount administered is physiologically significant. An agent is physiologically significant if its presence results in a detectable change in the physiology of a recipient mammal. In particular, an antibody preparation is physiologically significant if its presence invokes an antitumor response or mitigates the signs and symptoms of an autoimmune disease state. A physiologically significant effect could also be the evocation of a humoral and/or cellular immune response in the recipient mammal leading to modulation, growth inhibition or death of target cells.

DNL Based Bioactive Assemblies

Certain embodiments of the invention may concern bioactive assemblies that are built by a site-specific conjugation strategy based on the Dock-and-Lock (DNL) method. The DNL method exploits α-helical peptides that are found in nature to bind specifically with each other. The α-helical peptides are the dimerization and docking domain (DDD) in the regulatory (R) subunits of cAMP-dependent protein kinase (PKA) and the anchoring domain (AD) in various A-kinase anchoring proteins (AKAPs). By recombinantly fusing or chemically attaching each peptide to an entity of interest, these helices provide an excellent linker module for "docking" the two modified entities into a quasi-stable structure, which is further "locked" into a stable complex via the disulfide linkages formed from cysteine residues introduced into these helices. Two types of R subunits (RI and RII) are identified in PKA and each has α and β isoforms. Because the R subunits have been isolated only as stable dimers and AKAPs bind only to dimeric R subunits, a unique feature of the DNL method is that the entity derivatized with a peptide derived from the DDD always forms a homodimer, resulting in two copies of that entity in the final complex.

Two pairs of interacting DDD and AD peptides are of particular interest as the linker modules. The first pair consists of DDD2 (FIG. 1A, SEQ ID NO:1), derived from the 44-amino terminal residues of human RIIα, and AD2 (FIG. 1B, SEQ ID NO:2), derived from AKAP-IS, a synthetic peptide optimized for RIIα-selective binding (Alto et al., Proc Natl Acad Sci USA, 2003, 100: 4445-4450). The second pair consists of DDD3 (FIG. 1C, SEQ ID NO:3) or DDD3C (FIG. 1D, SEQ ID NO:4), derived from the peptide fragment (residues 12-61) of human RIα: (Leon et al., J Biol Chem, 1997, 272: 28431-28437), and AD3 (FIG. 1E, SEQ ID NO:5), derived from PV-38, a mutant peptide of D-AKAP2 that specifically binds to RIα (Burns-Hamuro et al, Proc Natl Acad Sci USA, 2003, 100: 4072-4077).

In one embodiment, a biological entity, referred to hereafter as the type-a adaptor module (Ma), containing two distinct AD peptides, one reacting preferentially with the DDD of RIIα (for example, AD2 with DDD2), and the other reacting preferentially with the DDD of RIα (for example, AD3 with DDD3C), is produced and used to complex with two other biological entities, referred to hereafter as the peripheral modules, one comprising a homodimer (designated as $X_2$) with each monomeric subunit linked to the DDD of RIIα and the other comprising a different homodimer (designated as $Y_2$) with each monomeric subunit linked to the DDD of RIα, resulting in an assembly of $X_2(Ma)Y_2$ that contains five individual components, as illustrated in FIG. 2.

Figure 3:
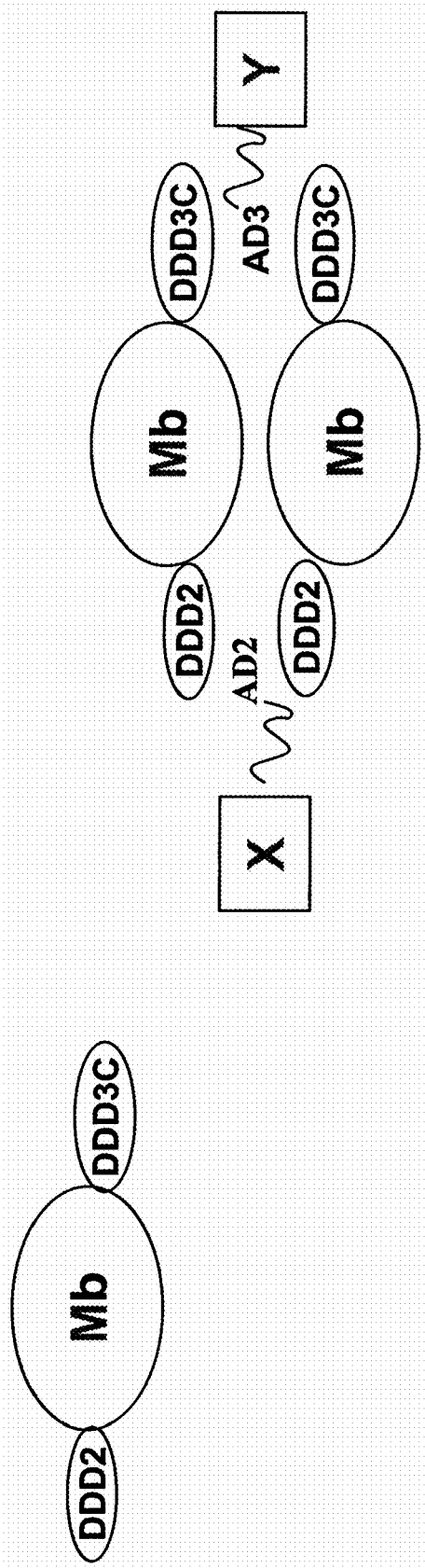
FIG. 3 shows a schematic diagram for an $X(Mb)_2Y$ bioactive assembly, based on a type-b adaptor molecule (Mb), for example attached to one molecule each of DDD2 and DDD3. Addition of appropriate anchoring domains, for example AD2 and AD3, that are attached to two different effector moieties results in dimerization and formation of the $X(Mb)_2Y$ assembly.

In another embodiment, a biological entity, referred to hereafter as the type-b adaptor module (Mb), which contains two distinct DDD peptides, one reacting preferentially with AD2 (for example, DDD2), and the other reacting preferentially with AD3 (for example DDD3C), is produced as a homodimer, referred to as $(Mb)_2$ hereafter, and used to complex with two peripheral modules, one comprising a monomeric subunit linked to AD2 (designated as X) and the other comprising a different monomeric subunit linked to AD3 (designated as Y), resulting in an assembly of $X(Mb)_2Y$ that contains four individual components, as illustrated in FIG. 3.

Figure 4:
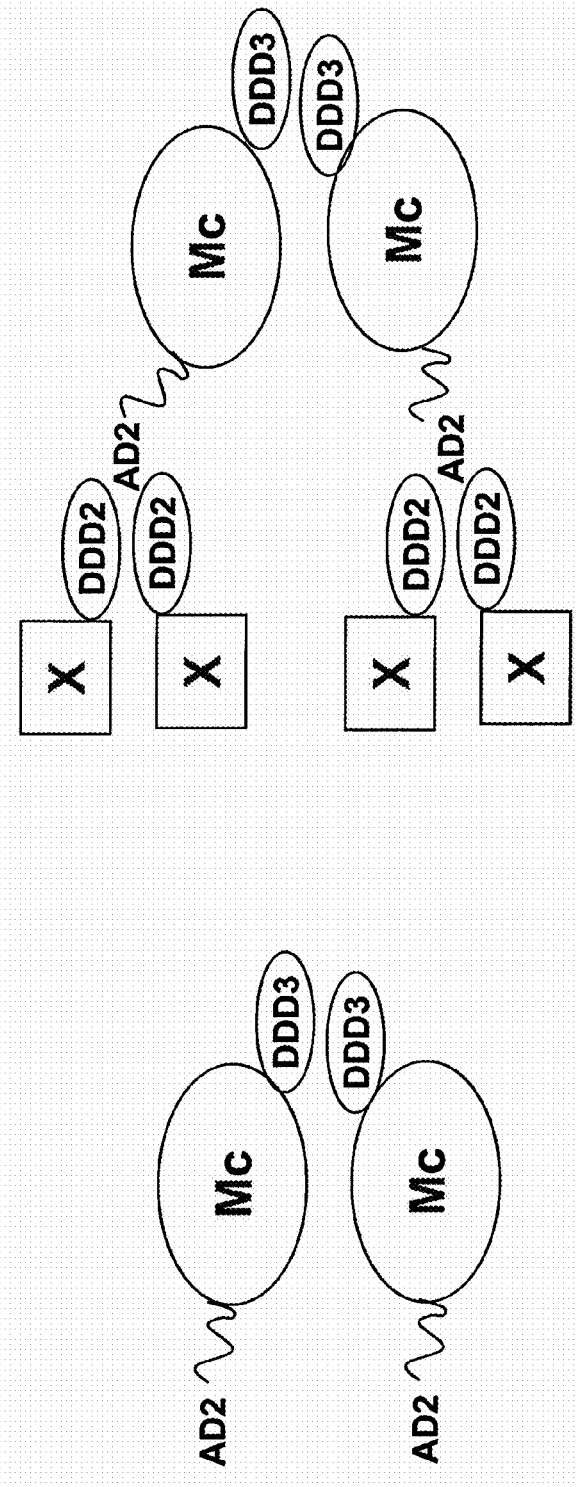
FIG. 4 shows a schematic diagram for an $X_2(Mc)_2X_2$ bioactive assembly, based on a type-c adaptor molecule (Mc), for example attached to one molecule each of DDD3 and AD2. Dimerization of the DDD3 sequences attached to different Mc molecules provides two anchoring sites (AD2) for binding of homodimers, each comprised of, for example, DDD2 attached to an effector X. The resulting bioactive assembly is a homotetramer comprising four copies of effector X.

In yet another embodiment, a biological entity, referred to hereafter as the type-c adaptor module (Mc), containing both AD2 and DDD3, is produced as a homodimer, referred to hereafter as $(Mc)_2$, and used to complex with two identical peripheral modules, each comprising a homodimer (designated as $X_2$) with individual monomeric subunit linked to DDD2, resulting in an assembly of $X_2(Mc)_2X_2$ that contains six individual components as illustrated in FIG. 4.

Figure 5:
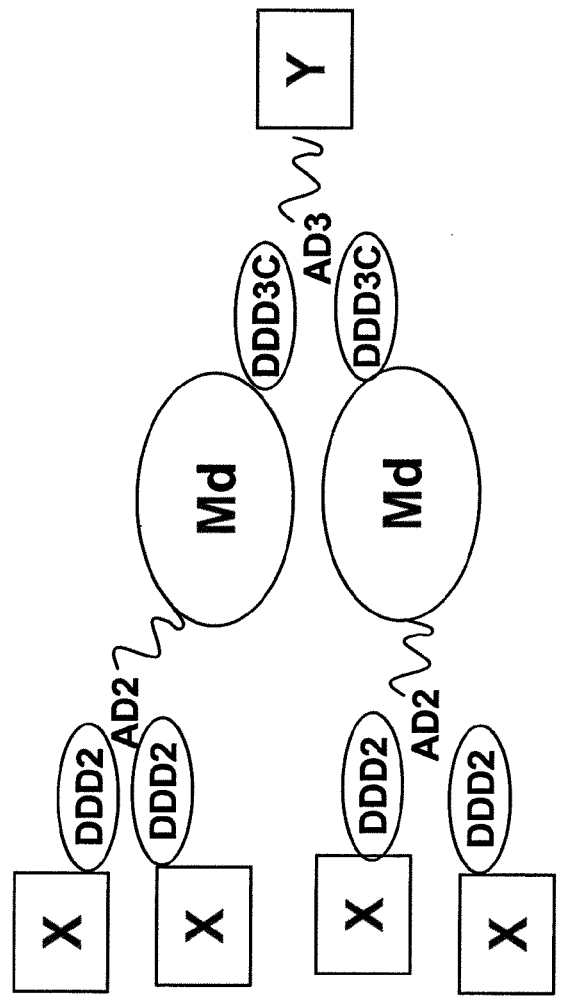
FIG. 5 shows a schematic diagram for an $X_2(Md)_{2'}X_2$ bioactive assembly, based on a type-d adaptor molecule (Md). The difference with the assembly shown in FIG. 4 is that a DDD3C dimerization and docking domain is used, allowing binding of an AD3 anchor domain attached to effector Y.

In a further embodiment, a biological entity, referred to as type-d adaptor module (Md) hereafter, which contains AD2 and DDD3C (instead of DDD3 as in type-c), is produced as a homodimer, referred to hereafter as $(Md)_2$, and used to complex three peripheral modules, two of which are identical homodimers (designated as $X_2$) with individual monomeric subunit linked to DDD2 and the third one consisting of a monomeric subunit linked to AD3 (designated as Y), resulting in an assembly of $X_2(Md)_2YX_2$ that contains seven individual components, as illustrated in FIG. 5.

In other embodiments, the bioactive assemblies produced by the present invention may be further conjugated with effectors and carriers to acquire additional functions enabled by such modifications. In addition, bioactive assemblies can be constructed to contain components capable of forming complexes with DNA or RNA, or synthetic oligodeoxynucleotides (ODN) containing the immunostimulatory CpG motifs (Klinman, Nat Rev Immunol, 2004, 4: 1-10; Krieg, Nat Rev Drug Discov, 2006, 5: 471-484).

Numerous bioactive assemblies can be designed and produced by the disclosed methods and compositions, with wide applications depending on which type of the adaptor module is selected and what peripheral modules are linked to the adaptor module. Bioactive entities that are of particular interest as the adaptor modules include the Fc of human IgG1, human serum albumin (HSA), various heat shock proteins (HSPs), bioluminescent proteins, human transferrin (hTf), and human protamines. Bioactive entities that may be derivatized to serve as peripheral modules include cytokines, chemokines, growth factors, soluble receptors, antibody fragments, fluorescent proteins, l-peptides, d-peptides, peptides containing unnatural amino acids, peptoids, peptomimetics, DNA sequences, synthetic CpG ODN, small interfering RNAs, human protamine 1, DNA-binding peptides derived from protamines, protein transduction domains, nuclear localization signals, peptides that facilitate transdermal delivery or membrane penetration, DNA or RNA aptamers, peptide aptamers, cholera toxin subunit B monomer, enzymes, polyethylene glycol, nanoparticles, drug-containing polymers, chelates, quantum dots, and various scaffold-based binding proteins such as Nanobody, Evibody, Ankyrin repeat protein, Trans-body, Anticalin, Microbody, AdNectin, Domain antibody, Affibody, Maxibody, Tetranectin, Affilin molecule, iMabs, and Monobody (Hey et al., Trends Biotechnol, 2005, 23: 514-522; Binz et al., Nat Biotechnol, 2005, 23: 1257-1268). Specific compositions of selected assemblies based on type-a, -b, -c, and -d adaptor modules are listed in Tables 1, 2, 3, and 4, respectively.

Adaptor modules based on HSPs. Subunit vaccines that consist of well-characterized molecules, although highly desirable due to their superior safety profile and ease of manufacturing, are hampered by their poor immunogenicity and limited stability, which may be remedied by the development of improved delivery vehicles as well as more efficacious yet nontoxic adjuvants. The present compositions and methods can be applied to generate subunit vaccines that (1) contain defined antigenic molecules, (2) have built-in adjuvants to enhance the immune response, and (3) are able to elicit an antigen-specific T cell immunity.

One approach is to generate type-a adaptor modules based on HSPs for linking to peripheral modules derived from target antigens and immune enhancers that are proteins or peptides, resulting in protein- or peptide-based vaccines for direct immunization or ex vivo priming of dendritic cells to achieve both MHC-I and MHC-II presentations (Srivastava, Nat Rev Immunol, 2002, 2: 185-194). Alternatively, the HSP-based adaptor modules are linked to peripheral modules derived from DNA-binding proteins, for example, human protamines (Song et al, Nat Biotechnol, 2005, 23: 709-717), or DNA-binding peptides containing clustered arginine residues, for example, RRRRRRGGRRRRRR (SEQ ID NO:10) (Brewer et al., J Biol Chem, 2003, 278: 42403-42406), and targeting molecules, for example, antibody fragments, resulting in multifunctional assemblies useful as target-specific DNA vaccines upon complexation with plasmids that encode the genes for target antigens or both target antigens and immune enhancers. Further expansion of the spectrum for broader protection by such vaccines is also feasible due to the ability of HSPs to noncovalently associate with a variety of antigenic peptides (U.S. Pat. No. 5,935,576; U.S. Pat. No. 5,750,119). Example 1 describes the generation and use of type-a adaptor modules based on HSPs.

Adaptor modules based on human protamines. Bioactive assemblies that use adaptors modules based on human protamines are particularly suitable for delivery of DNA vaccines, siRNAs, or therapeutic genes to specific cells. A fusion protein (F105-P) consisting of anti-gp120 Fab and human protamine 1 (hP1) has been shown to be effective in delivering plasmids encoding Pesudomonas exotoxin A (Chen et al., Gene Ther, 1995, 2: 116-123) or siRNAs to HIV-infected cells or HIV envelope-expressing tumor cells (Song et al, Nat Biotechnol, 2005, 23: 709-717). Type-b adaptor modules based on hP1 can be generated for linking to peripheral modules derived from different biological entities, such as target specific binding proteins, and the resulting assembly is used as a carrier for target specific delivery of plasmids or siRNAs, which are bound to hP1 by complexation. Alternatively, type-c adaptor modules based on hP1 can be generated for linking to peripheral modules derived from the same biological entity, such as target specific binding proteins, and the resulting assembly, which contains four copies of the target specific binding proteins, is used as a carrier for target specific delivery of plasmids or siRNAs, which are bound to hP1 by complexation. A further embodiment is to generate type-d adaptor modules based on hP1 for linking to peripheral modules derived from two different biological entities and the resulting assembly, which contains four copies of one entity and one copy of the other entity is used as a carrier for plasmids or siRNAs, which are bound to hP1 by complexation. Examples 2 and 3 describe the generation and use of type-b and -c adaptor modules based on hP1, respectively.

Adaptor modules based on the Fc of human immunoglobulins. Fusion proteins containing the Fc of human IgG have many advantages conferred by the innate properties of the Fc. For example, binding of the Fc to the neonatal receptor (FcRn) expressed on lung and intestine epithelium facilitates transport of Fc-fusion proteins across the mucosal barriers (Spiekermann et al., J Exp Med, 2002, 196: 303-310), thus making pulmonary or oral delivery feasible (Dumont et al., J Aerosol Med, 2005, 18: 294-303; Bitonti et al., Proc Natl Acad Sci USA, 2004, 101: 9763-9768; Low et al., Hum Reprod, 2005, 20: 1805-1813). The pH-dependent binding of the Fc to the FcRn expressed in continuous capillary endothelium also prolongs the serum half-lives of IgG antibodies or Fc-containing fusion proteins. IgG or Fc mutants with higher affinity for the FcRn were shown to substantially increase the serum half-lives of such engineered constructs (Hinton et al., J Immunol, 2006, 176: 346-356; Hinton et al., J Biol Chem, 2004, 279: 6213-6216). On the other hand, IgG or Fc mutants with lower affinity for the FcRn exhibited shorter serum half-lives compared to the corresponding wild types (Kenanova et al., Cancer Res, 2005, 65: 622-631). The ability to tailor the pharmacokinetics of a biological entity containing Fc is very attractive for drug design. The generation and use of type-b, -c, and -d adaptor modules based on the Fc are outlined in Examples 4, 5, and 6, respectively. Detailed methods of constructing the expression vectors for DDD3-CH2-CH3-AD2 and DDD3C—CH2-CH3-AD2 are described in Example 7.

Conjugates of Bioactive Assemblies

Additional moieties can be conjugated to the bioactive assemblies described above. For example, drugs, toxins, radioactive compounds, enzymes, hormones, cytotoxic proteins, chelates, cytokines, and other functional agents may be conjugated to the bioactive assemblies. Conjugation can be via, for example, covalent attachments to amino acid residues containing amine, carboxyl, thiol or hydroxyl groups in the side-chains. Various conventional linkers may be used for this purpose, for example, diisocyanates, diisothiocyanates, bis (hydroxysuccinimide) esters, carbodiimides, maleimide-hydroxysuccinimide esters, glutaraldehyde and the like. Conjugation of agents to the bioactive assemblies preferably does not significantly affect the activity of each subunit contained in the unmodified structures. Conjugation can be carried out separately to the different peripheral modules and the resulting conjugates used for preparing the bioactive assemblies. In addition, cytotoxic agents may be first coupled to a polymeric carrier, which is then conjugated to a bioactive assembly. For this method, see Ryser et al., *Proc. Natl. Acad. Sci. USA*, 75:3867-3870, 1978; U.S. Pat. No. 4,699,784 and U.S. Pat. No. 4,046,722, which are incorporated herein by reference. As discussed below, one or more effectors may also be conjugated to a carrier moiety, which may then be targeted to a bioactive assembly by incorporation into the assembly of, for example, a monoclonal antibody or fragment that binds specifically to the carrier moiety. An exemplary use of carrier moieties for delivery of effector molecules to bioactive assemblies localized to a targeted cell, tissue or pathogenic organism is described below in the pre-targeting section.

The conjugates described herein can be prepared by various methods known in the art. For example, a bioactive assembly can be radiolabeled with $^{131}$I and conjugated to a lipid, such that the resulting conjugate can form a liposome. The liposome may incorporate one or more therapeutic (e.g., a drug such as FUdR-dO) or diagnostic agents. Alternatively, in addition to the carrier, a bioactive assembly may be conjugated to $^{131}$I (e.g., at a tyrosine residue) and a drug (e.g., at the epsilon amino group of a lysine residue), and the carrier may incorporate an additional therapeutic or diagnostic agent. Therapeutic and diagnostic agents may be covalently associated with one or more than one subunit of the bioactive assemblies.

The formation of liposomes and micelles is known in the art. See, e.g., Wrobel and Collins, Biochimica et Biophysica Acta (1995), 1235: 296-304; Lundberg et al., J. Pharm. Pharmacol. (1999), 51:1099-1105; Lundberg et al., Int. J. Pharm. (2000), 205:101-108; Lundberg, J. Pharm. Sci. (1994), 83:72-75; Xu et al., Molec. Cancer Ther. (2002), 1:337-346; Torchilin et al., Proc. Nat'l. Acad. Sci., U.S.A. (2003), 100: 6039-6044; U.S. Pat. No. 5,565,215; U.S. Pat. No. 6,379,698; and U.S. 2003/0082154.

Nanoparticles or nanocapsules formed from polymers, silica, or metals, which are useful for drug delivery or imaging, have been described as well. See, e.g., West et al., Applications of Nanotechnology to Biotechnology (2000), 11:215-217; U.S. Pat. No. 5,620,708; U.S. Pat. No. 5,702,727; and U.S. Pat. No. 6,530,944. The conjugation of antibodies or binding molecules to liposomes to form a targeted carrier for therapeutic or diagnostic agents has been described. See, e.g., Bendas, Biodrugs (2001), 15:215-224; Xu et al., Mol. Cancer. Ther (2002), 1:337-346; Torchilin et al., Proc. Nat'l. Acad. Sci. U.S.A (2003), 100:6039-6044; Bally, et al., J. Liposome Res. (1998), 8:299-335; Lundberg, Int. J. Pharm. (1994), 109:73-81; Lundberg, J. Pharm. Pharmacol. (1997), 49:16-21; Lundberg, Anti-cancer Drug Design (1998), 13: 453-461. See also U.S. Pat. No. 6,306,393; U.S. Ser. No. 10/350,096; U.S. Ser. No. 09/590,284, and U.S. Ser. No. 60/138,284, filed Jun. 9, 1999. All these references are incorporated herein by reference.

A wide variety of diagnostic and therapeutic agents can be advantageously used to form the conjugates of the bioactive assemblies, or may be linked to haptens that bind to a recognition site on the bioactive assemblies. Diagnostic agents may include radioisotopes, enhancing agents for use in MRI or contrast agents for ultrasound imaging, and fluorescent compounds. Many appropriate imaging agents are known in the art, as are methods for their attachment to proteins or peptides (see, e.g., U.S. Pat. Nos. 5,021,236 and 4,472,509, both incorporated herein by reference). Certain attachment methods involve the use of a metal chelate complex employing, for example, an organic chelating agent such a DTPA attached to the protein or peptide (U.S. Pat. No. 4,472,509).

In order to load a bioactive assembly with radioactive metals or paramagnetic ions, it may be necessary to first react it with a carrier to which multiple copies of a chelating group for binding the radioactive metals or paramagnetic ions have been attached. Such a carrier can be a polylysine, polysaccharide, or a derivatized or derivatizable polymeric substance having pendant groups to which can be bound chelating groups such as, e.g., ethylenediaminetetraacetic acid (EDTA), diethylenetriaminepentaacetic acid (DTPA), porphyrins, polyamines, crown ethers, bis-thiosemicarbazones, polyoximes, and the like known to be useful for this purpose. Carriers containing chelates are coupled to the bioactive assembly using standard chemistries in a way to minimize aggregation and loss of immunoreactivity.

Other methods and reagents that may be applied for preparing such conjugates are disclosed in U.S. Pat. No. 4,824,659, which is incorporated herein in its entirety by reference. Particularly useful metal-chelate combinations include 2-benzyl-DTPA and its monomethyl and cyclohexyl analogs, used with diagnostic isotopes in the general energy range of 60 to 4,000 keV. Some useful diagnostic nuclides may include $^{124}$I, $^{18}$F, $^{52}$Fe, $^{62}$Cu, $^{64}$Cu, $^{67}$Cu, $^{67}$Ga, $^{68}$Ga, $^{86}$Y, $^{89}$Zr, $^{94}$Tc, $^{94m}$Tc, $^{99m}$Tc, or $^{111}$In. The same chelates complexed with non-radioactive metals, such as manganese, iron and gadolinium, are useful for MRI, when used along with the bioactive assemblies and carriers described herein. Macrocyclic chelates such as NOTA, DOTA, and TETA are of use with a variety of metals and radiometals, most particularly with radionuclides of gallium, yttrium and copper, respectively. Such metal-chelate complexes can be made very stable by tailoring the ring size to the metal of interest. Other ring-type chelates, such as macrocyclic polyethers for complexing $^{223}$Ra, may be used.

Therapeutic agents include, for example, chemotherapeutic drugs such as vinca alkaloids, anthracyclines, epidophyllotoxins, taxanes, antimetabolites, alkylating agents, antibiotics, Cox-2 inhibitors, antimitotics, antiangiogenic and proapoptotic agents, particularly doxorubicin, methotrexate, taxol, CPT-11, SN-38, camptothecans, and others from these and other classes of anticancer agents, and the like. Other cancer chemotherapeutic drugs include nitrogen mustards, alkyl sulfonates, nitrosoureas, triazenes, folic acid analogs, pyrimidine analogs, purine analogs, platinum coordination complexes, hormones, and the like. Suitable chemotherapeutic agents are described in REMINGTON'S PHARMACEUTICAL SCIENCES, 19th Ed. (Mack Publishing Co. 1995), and in GOODMAN AND GILMAN'S THE PHARMACOLOGICAL BASIS OF THERAPEUTICS, 7th Ed. (MacMillan Publishing Co. 1985), as well as revised editions of these publications. Other suitable chemotherapeutic agents, such as experimental drugs, are known to those of skill in the art, and may be conjugated to the bioactive assemblies described herein using methods that are known in the art.

Another class of therapeutic agents consists of radionuclides that emit α-particles (such as $^{212}$Pb, $^{212}$Bi, $^{213}$Bi, $^{211}$At, $^{223}$Ra, $^{225}$Ac), β-particles (such as $^{32}$P, $^{33}$P, $^{47}$Sc, $^{67}$Cu, $^{67}$Ga, $^{89}$Sr, $^{90}$Y, $^{111}$Ag, $^{125}$I, $^{131}$I, $^{142}$Pr, $^{153}$Sm, $^{161}$Tb, $^{166}$Ho, $^{166}$Dy, $^{177}$Lu, $^{186}$Re, $^{188}$Re, $^{189}$Re), or Auger electrons (such as $^{111}$In, $^{125}$I, $^{67}$Ga, $^{191}$Os, $^{193m}$Pt, $^{195m}$Pt, $^{195m}$Hg). The bioactive assemblies may be labeled with one or more of the above radionuclides using methods as described for the diagnostic agents.

Exemplary therapeutic peptides or proteins of use as effectors are disclosed in U.S. Pat. No. 6,309,633 (incorporated herein by reference) and may include, for example: adrenocorticotropic hormone (ACTH); adrenocorticotropic hormone derivatives (e.g., ebiratide); angiotensin; angiotensin II; asparaginase; atrial natriuretic peptides; atrial sodium diuretic peptides; bacitracin; beta-endorphins; blood coagulation factors VII, VIII and IX; blood thymic factor (FTS); blood thymic factor derivatives (see U.S. Pat. No. 4,229,438); bombesin; bone morphogenic factor (BMP); bone morphogenic protein; bradykinin; caerulein; calcitonin gene related polypeptide (CGRP); calcitonins; CCK-8; cell growth factors (e.g., EGF; TGF-alpha; TGF-beta; PDGF; acidic FGF; basic FGF); cerulein; chemokines; cholecystokinin; cholecystokinin-8; cholecystokinin-pancreozymin (CCK-PZ); colistin; colony-stimulating factors (e.g. CSF; GCSF; GMCSF; MCSF); corticotropin-releasing factor (CRF); cytokines; desmopressin; dinorphin; dipeptide; dismutase; dynorphin; eledoisin; endorphins; endothelin; endothelin-antagonistic peptides (see European Patent Publication Nos. 436189; 457195 and 496-452 and Japanese Patent Unexamined Publication Nos. 94692/1991 and 130299/1991); endotherins; enkephalins; enkephalin derivatives (see U.S. Pat. No. 4,277, 394 and European Patent Publication No. 31567); epidermal growth factor (EGF); erythropoietin (EPO); follicle-stimulating hormone (FSH); gallanin; gastric inhibitory polypeptide; gastrin-releasing polypeptide (GRP); gastrins; G-CSF; glucagon; glutathione peroxidase; glutathio-peroxidase; gonadotropins (e.g., human chorionic gonadotrophin and .alpha. and .beta. subunits thereof); gramicidin; gramicidines; growth factor (EGF); growth hormone-releasing factor (GRF); growth hormones; hormone releasing hormone (LHRH); human artrial natriuretic polypeptide (h-ANP); human placental lactogen; insulin; insulin-like growth factors (IGF-I; IGF-II); interferon; interferons (e.g., alpha- beta- and gamma-interferons); interleukins (e.g. 1; 2; 3; 4; 5; 6; 7; 8; 9; 10; 11 and 12); intestinal polypeptide (VIP); kallikrein; kyotorphin; luliberin; luteinizing hormone (LH); luteinizing hormone-releasing hormone (LH-RH); lysozyme chloride; melanocyte-stimulating hormone (MSH); melanophore stimulating hormone; mellitin; motilin; muramyl; muramyl-dipeptide; nerve growth factor (NGF); nerve nutrition factors (e.g. NT-3; NT-4; CNTF; GDNF; BDNF); neuropeptide Y; neurotensin; oxytocin; pancreastatin; pancreatic polypeptide; pancreozymin; parathyroid hormone (PTH); pentagastrin; polypeptide YY; pituitary adenyl cyclase-activating polypeptides (PACAPs); platelet-derived growth factor; polymixin B; prolactin; protein synthesis stimulating polypeptide; PTH-related protein; relaxin; renin; secretin; serum thymic factor; somatomedins; somatostatins derivatives (Sandostatin; see U.S. Pat. Nos. 4,087,390; 4,093,574; 4,100,117 and 4,253, 998); substance P; superoxide dismutase; taftsin; tetragastrin; thrombopoietin (TPO); thymic humoral factor (THF); thymopoietin; thymosin; thymostimulin; thyroid hormone releasing hormone; thyroid-stimulating hormone (TSH); thyrotropin releasing hormone TRH); trypsin; tuftsin; tumor growth factor (TGF-alpha); tumor necrosis factor (TNF); tyrocidin; urogastrone; urokinase; vasoactive intestinal polypeptide; vasopressins, and functional equivalents of such polypeptides.

A suitable peptide containing a detectable label (e.g., a fluorescent molecule), or a cytotoxic agent, (e.g., a radioiodine), can be covalently, non-covalently, or otherwise associated with the bioactive assemblies. For example, a therapeutically useful conjugate can be obtained by incorporating a photoactive agent or dye onto the bioactive assemblies. Fluorescent compositions, such as fluorochrome, and other chromogens, or dyes, such as porphyrins sensitive to visible light, have been used to detect and to treat lesions by directing the suitable light to the lesion. In therapy, this has been termed photoradiation, phototherapy, or photodynamic therapy. See Jori et al. (eds.), PHOTODYNAMIC THERAPY OF TUMORS AND OTHER DISEASES (Libreria Progetto 1985); van den Bergh, Chem. Britain (1986), 22:430. Moreover, monoclonal antibodies have been coupled with photoactivated dyes for achieving phototherapy. See Mew et al., J. Immunol. (1983), 130:1473; idem., Cancer Res. (1985), 45:4380; Oseroff et al., Proc. Natl. Acad. Sci. USA (1986), 83:8744; idem., Photochem. Photobiol. (1987), 46:83; Hasan et al., Prog. Clin. Biol. Res. (1989), 288:471; Tatsuta et al., Lasers Surg. Med. (1989), 9:422; Pelegrin et al., Cancer (1991), 67:2529. Endoscopic applications are also contemplated. Endoscopic methods of detection and therapy are described in U.S. Pat. No. 4,932,412; U.S. Pat. No. 5,525, 338; U.S. Pat. No. 5,716,595; U.S. Pat. No. 5,736,119; U.S. Pat. No. 5,922,302; U.S. Pat. No. 6,096,289; and U.S. Pat. No. 6,387,350, which are incorporated herein by reference in their entirety.

In certain embodiments, the novel constructs and methods disclosed herein are useful for targeted delivery of RNAi for therapeutic intervention. The delivery vehicle can be a bioactive assembly with an internalizing antibody binding domain fused to human protamine (peptide of 50 amino acid residues). An example would be an assembly comprising human protamine 1 (hP1) and/or human protamine 2 (hP2), both capable of forming stable DNA or RNA complexes such as RNAi for in vivo applications (Nat Biotechnol. 23: 709-717, 2005; Gene Therapy. 13: 194-195, 2006). The multivalent complex will facilitate the binding to and receptor-mediated internalization into target cells, where the noncovalently bound RNAi is dissociated in the endosomes and released into cytoplasm. In addition to delivery of RNAi, these constructs may also be of use for targeted delivery of therapeutic genes or DNA vaccines. Another area of use is to apply the technology for producing intrabodies, which is the protein analog of RNAi in terms of function.

Peptide Administration

Various embodiments of the claimed methods and/or compositions may concern one or more peptide based bioactive assemblies to be administered to a subject. Administration may occur by any route known in the art, including but not limited to oral, nasal, buccal, inhalational, rectal, vaginal, topical, orthotopic, intradermal, subcutaneous, intramuscular, intraperitoneal, intraarterial, intrathecal or intravenous injection.

Unmodified peptides administered orally to a subject can be degraded in the digestive tract and depending on sequence and structure may exhibit poor absorption across the intestinal lining. However, methods for chemically modifying peptides to render them less susceptible to degradation by endogenous proteases or more absorbable through the alimentary tract are well known (see, for example, Blondelle et al., 1995, Biophys. J. 69:604-11; Ecker and Crooke, 1995, Biotechnology 13:351-69; Goodman and Ro, 1995, BURGER'S MEDICINAL CHEMISTRY AND DRUG DISCOVERY, VOL. 1, ed. Wollf, John Wiley & Sons; Goodman and Shao, 1996, Pure & Appl. Chem. 68:1303-08). Methods for preparing libraries of peptide analogs, such as peptides containing D-amino acids; peptidomimetics consisting of organic molecules that mimic the structure of a peptide; or peptoids such as vinylogous peptoids, have also been described and may be used to construct peptide based bioactive assemblies suitable for oral administration to a subject.

In certain embodiments, the standard peptide bond linkage may be replaced by one or more alternative linking groups, such as $CH_2$—NH, $CH_2$—S, $CH_2$—$CH_2$, CH=CH, CO—$CH_2$, CHOH—$CH_2$ and the like. Methods for preparing peptide mimetics are well known (for example, Hruby, 1982, *Life Sci* 31:189-99; Holladay et al., 1983, *Tetrahedron Lett.* 24:4401-04; Jennings-White et al., 1982, *Tetrahedron Lett.* 23:2533; Almquiest et al., 1980, *J. Med. Chem.* 23:1392-98; Hudson et al., 1979, *Int. J. Pept. Res.* 14:177-185; Spatola et al., 1986, *Life Sci* 38:1243-49; U.S. Pat. Nos. 5,169,862; 5,539,085; 5,576,423, 5,051,448, 5,559,103, each incorporated herein by reference.) Peptide mimetics may exhibit enhanced stability and/or absorption in vivo compared to their peptide analogs.

Alternatively, peptides may be administered by oral delivery using N-terminal and/or C-terminal capping to prevent exopeptidase activity. For example, the C-terminus may be capped using amide peptides and the N-terminus may be capped by acetylation of the peptide. Peptides may also be cyclized to block exopeptidases, for example by formation of cyclic amides, disulfides, ethers, sulfides and the like.

Peptide stabilization may also occur by substitution of D-amino acids for naturally occurring L-amino acids, particularly at locations where endopeptidases are known to act. Endopeptidase binding and cleavage sequences are known in the art and methods for making and using peptides incorporating D-amino acids have been described (e.g., U.S. Patent Application Publication No. 20050025709, McBride et al., filed Jun. 14, 2004, incorporated herein by reference). In certain embodiments, peptides and/or proteins may be orally administered by co-formulation with proteinase- and/or peptidase-inhibitors.

Other methods for oral delivery of therapeutic peptides are disclosed in Mehta ("Oral delivery and recombinant production of peptide hormones," June 2004, *BioPharm International*). The peptides are administered in an enteric-coated solid dosage form with excipients that modulate intestinal proteolytic activity and enhance peptide transport across the intestinal wall. Relative bioavailability of intact peptides using this technique ranged from 1% to 10% of the administered dosage. Insulin has been successfully administered in dogs using enteric-coated microcapsules with sodium cholate and a protease inhibitor (Ziv et al., 1994, *J. Bone Miner. Res.* 18 (Suppl. 2):792-94. Oral administration of peptides has been performed using acylcarnitine as a permeation enhancer and an enteric coating (Eudragit L30D-55, Rohm Pharma Polymers, see Mehta, 2004). Excipients of use for orally administered peptides may generally include one or more inhibitors of intestinal proteases/peptidases along with detergents or other agents to improve solubility or absorption of the peptide, which may be packaged within an enteric-coated capsule or tablet (Mehta, 2004). Organic acids may be included in the capsule to acidify the intestine and inhibit intestinal protease activity once the capsule dissolves in the intestine (Mehta, 2004). Another alternative for oral delivery of peptides would include conjugation to polyethylene glycol (PEG)-based amphiphilic oligomers, increasing absorption and resistance to enzymatic degradation (Soltero and Ekwuribe, 2001, *Pharm. Technol.* 6:110).

In still other embodiments, peptides may be modified for oral or inhalational administration by conjugation to certain proteins, such as the Fc region of IgG1 (see Examples 3-7). Methods for preparation and use of peptide-Fc conjugates are disclosed, for example, in Low et al. (2005, *Hum. Reprod.* 20:1805-13) and Dumont et al. (2005, *J. Aerosol Med.* 18:294-303), each incorporated herein by reference. Low et al. (2005) disclose the conjugation of the alpha and beta subunits of FSH to the Fc region of IgG1 in single chain or heterodimer form, using recombinant expression in CHO cells. The Fc conjugated peptides were absorbed through epithelial cells in the lung or intestine by the neonatal Fc receptor mediated transport system. The Fc conjugated peptides exhibited improved stability and absorption in vivo compared to the native peptides. It was also observed that the heterodimer conjugate was more active than the single chain form.

Proteins and Peptides

A variety of polypeptides or proteins may be used within the scope of the claimed methods and compositions. In certain embodiments, the proteins may comprise antibodies or fragments of antibodies containing an antigen-binding site. As used herein, a protein, polypeptide or peptide generally refers, but is not limited to, a protein of greater than about 200 amino acids, up to a full length sequence translated from a gene; a polypeptide of greater than about 100 amino acids; and/or a peptide of from about 3 to about 100 amino acids. For convenience, the terms "protein," "polypeptide" and "peptide" are used interchangeably herein. Accordingly, the term "protein or peptide" encompasses amino acid sequences comprising at least one of the 20 common amino acids found in naturally occurring proteins, or at least one modified or unusual amino acid.

As used herein, an "amino acid residue" refers to any naturally occurring amino acid, any amino acid derivative or any amino acid mimic known in the art. In certain embodiments, the residues of the protein or peptide are sequential, without any non-amino acid interrupting the sequence of amino acid residues. In other embodiments, the sequence may comprise one or more non-amino acid moieties. In particular embodiments, the sequence of residues of the protein or peptide may be interrupted by one or more non-amino acid moieties.

Accordingly, the term "protein or peptide" encompasses amino acid sequences comprising at least one of the 20 common amino acids found in naturally occurring proteins, or at least one modified or unusual amino acid, including but not limited to those shown below.

| Modified and Unusual Amino Acids | |
|---|---|
| Abbr. | Amino Acid |
| Aad | 2-Aminoadipic acid |
| Baad | 3-Aminoadipic acid |
| Bala | β-alanine, β-Amino-propionic acid |
| Abu | 2-Aminobutyric acid |
| 4Abu | 4-Aminobutyric acid, piperidinic acid |
| Acp | 6-Aminocaproic acid |
| Ahe | 2-Aminoheptanoic acid |
| Aib | 2-Aminoisobutyric acid |
| Baib | 3-Aminoisobutyric acid |
| Apm | 2-Aminopimelic acid |
| Dbu | 2,4-Diaminobutyric acid |
| Des | Desmosine |
| Dpm | 2,2'-Diaminopimelic acid |
| Dpr | 2,3-Diaminopropionic acid |
| EtGly | N-Ethylglycine |
| EtAsn | N-Ethylasparagine |
| Hyl | Hydroxylysine |
| AHyl | allo-Hydroxylysine |
| 3Hyp | 3-Hydroxyproline |
| 4Hyp | 4-Hydroxyproline |
| Ide | Isodesmosine |
| AIle | allo-Isoleucine |
| MeGly | N-Methylglycine, sarcosine |
| MeIle | N-Methylisoleucine |
| MeLys | 6-N-Methyllysine |
| MeVal | N-Methylvaline |
| Nva | Norvaline |
| Nle | Norleucine |
| Orn | Ornithine |

Proteins or peptides may be made by any technique known to those of skill in the art, including the expression of proteins, polypeptides or peptides through standard molecular biological techniques, the isolation of proteins or peptides from natural sources, or the chemical synthesis of proteins or peptides. The nucleotide and protein, polypeptide and peptide sequences corresponding to various genes have been previously disclosed and may be found at computerized databases known to those of ordinary skill in the art. One such database is the National Center for Biotechnology Information's Genbank and GenPept databases (www.ncbi.nlm.nih.gov/). The coding regions for known genes may be amplified and/or expressed using the techniques disclosed herein or as would be know to those of ordinary skill in the art. Alternatively, various commercial preparations of proteins, polypeptides, and peptides are known to those of skill in the art.

Peptide Mimetics

Another embodiment for the preparation of polypeptides is the use of peptide mimetics. Mimetics are peptide-containing molecules that mimic elements of protein secondary structure. See, for example, Johnson et al., "Peptide Turn Mimetics" in *BIOTECHNOLOGY AND PHARMACY*, Pezzuto et al, Eds., Chapman and Hall, New York (1993), incorporated herein by reference. The rationale behind the use of peptide mimetics is that the peptide backbone of proteins exists chiefly to orient amino acid side chains so as to facilitate molecular interactions, such as those of antibody and antigen. A peptide mimetic is expected to permit molecular interactions similar to the natural molecule.

Fusion Proteins

Various embodiments may concern fusion proteins. These molecules generally have all or a substantial portion of a peptide, linked at the N- or C-terminus, to all or a portion of a second polypeptide or protein. Methods of generating fusion proteins are well known to those of skill in the art. Such proteins may be produced, for example, by chemical attachment using bifunctional cross-linking reagents, by de novo synthesis of the complete fusion protein, or by attachment of a DNA sequence encoding a first protein or peptide to a DNA sequence encoding a second peptide or protein, followed by expression of the intact fusion protein.

Synthetic Peptides

Proteins or peptides may be synthesized, in whole or in part, in solution or on a solid support in accordance with conventional techniques. Various automatic synthesizers are commercially available and can be used in accordance with known protocols. See, for example, Stewart and Young, (1984, *Solid Phase Peptide Synthesis*, 2d. ed., Pierce Chemical Co.); Tam et al., (1983, *J. Am. Chem. Soc.*, 105:6442); Merrifield, (1986, *Science*, 232: 341-347); and Barany and Merrifield (1979, *The Peptides*, Gross and Meienhofer, eds., Academic Press, New York, pp. 1-284). Short peptide sequences, usually from about 6 up to about 35 to 50 amino acids, can be readily synthesized by such methods. Alternatively, recombinant DNA technology may be employed wherein a nucleotide sequence which encodes a peptide of interest is inserted into an expression vector, transformed or transfected into an appropriate host cell, and cultivated under conditions suitable for expression.

Antibodies

Various embodiments may concern antibodies for a target. The term "antibody" is used herein to refer to any antibody-like molecule that has an antigen binding region, and includes antibody fragments such as Fab', Fab, F(ab')$_2$, single domain antibodies (DABs), Fv, scFv (single chain Fv), and the like. Techniques for preparing and using various antibody-based constructs and fragments are well known in the art. Means for preparing and characterizing antibodies are also well known in the art (See, e.g., Harlowe and Lane, 1988, *Antibodies: A Laboratory Manual*, Cold Spring Harbor Laboratory). Antibodies of use may also be commercially obtained from a wide variety of known sources. For example, a variety of antibody secreting hybridoma lines are available from the American Type Culture Collection (ATCC, Manassas, Va.). A large number of antibodies against various disease targets, including but not limited to tumor-associated antigens, have been deposited at the ATCC and are available for use in the claimed methods and compositions. (See, for example, U.S. Pat. Nos. 7,060,802; 7,056,509; 7,049,060; 7,045,132; 7,041,803; 7,041,802; 7,041,293; 7,038,018; 7,037,498; 7,012,133; 7,001,598; 6,998,468; 6,994,976; 6,994,852; 6,989,241; 6,974,863; 6,965,018; 6,964,854; 6,962,981; 6,962,813; 6,956,107; 6,951,924; 6,949,244; 6,946,129; 6,943,020; 6,939,547; 6,921,645; 6,921,645; 6,921,533; 6,919,433; 6,919,078; 6,916,475; 6,905,681; 6,899,879; 6,893,625; 6,887,468; 6,887,466; 6,884,594; 6,881,405; 6,878,812; 6,875,580; 6,872,568; 6,867,006; 6,864,062; 6,861,511; 6,861,227; 6,861,226; 6,838,282; 6,835,549; 6,835,370; 6,824,780; 6,824,778; 6,812,206; 6,793,924; 8,783,758; 6,770,450; 6,767,711; 6,764,681; 6,764,679; 6,743,898;

6,733,981; 6,730,307; 6,720,15; 6,716,966; 6,709,653; 6,693,176; 6,692,908; 6,689,607; 6,689,362; 6,689,355; 6,682,737; 6,682,736; 6,682,734; 6,673,344; 6,652,852; 6,635,482; 6,630,144; 6,610,833; 6,610,294; 6,605,441; 6,605,279; 6,596,852; 6,592,868; 6,576,745; 6,572,856; 6,566,076; 6,562,618; 6,545,130; 6,544,749; 6,534,058; 6,528,625; 6,528,269; 6,521,227; 6,518,404; 6,511,665; 6,491,915; 6,488,930; 6,482,598; 6,482,408; 6,479,247; 6,468,531; 6,468,529; 6,465,173; 6,461,823; 6,458,356; 6,455,044; 6,455,040, 6,451,310; 6,444,206' 6,441,143; 6,432,404; 6,432,402; 6,419,928; 6,413,726; 6,406,694; 6,403,770; 6,403,091; 6,395,274; 6,383,759; 6,383,484; 6,376,654; 6,372,215; 6,359,126; 6,355,481; 6,355,444; 6,355,245; 6,355,244; 6,346,246; 6,344,198; 6,340,571; 6,340,459 each incorporated herein by reference with respect to the ATCC deposit number for the antibody-secreting hybridoma cell lines and the associated target antigens for the antibodies or fragments thereof.) These are exemplary only and a wide variety of other antibody-secreting hybridomas are known in the art. The skilled artisan will realize that antibody-secreting hybridomas against almost any disease-associated antigen may be obtained by a simple search of the ATCC, PubMed and/or USPTO databases for antibodies against the selected disease-associated target of interest.

Production of Antibody Fragments

Some embodiments of the claimed methods and/or compositions may concern antibody fragments. Such antibody fragments may be obtained by pepsin or papain digestion of whole antibodies by conventional methods. For example, antibody fragments may be produced by enzymatic cleavage of antibodies with pepsin to provide F(ab')$_2$ fragments. This fragment may be further cleaved using a thiol reducing agent and, optionally, followed by a blocking group for the sulfhydryl groups resulting from cleavage of disulfide linkages, to produce Fab' monovalent fragments. Alternatively, an enzymatic cleavage using papain n produces two monovalent Fab fragments and an Fe fragment. Exemplary methods for producing antibody fragments are disclosed in U.S. Pat. No. 4,036,945; U.S. Pat. No. 4,331,647; Nisonoff et al., 1960, Arch. Biochem. Biophys., 89:230; Porter, 1959, Biochem. J., 73:119; Edelman et al., 1967, METHODS IN ENZYMOLOGY, page 422 (Academic Press), and Coligan et al. (eds.), 1991, CURRENT PROTOCOLS IN IMMUNOLOGY, (John Wiley & Sons).

Other methods of cleaving antibodies, such as separation of heavy chains to form monovalent light-heavy chain fragments, further cleavage of fragments or other enzymatic, chemical or genetic techniques also may be used, so long as the fragments bind to the antigen that is recognized by the intact antibody. For example, Fv fragments comprise an association of $V_H$ and $V_L$ chains. This association can be noncovalent, as described in Inbar et al., 1972, Proc. Nat'l. Acad. Sci. USA, 69:2659. Alternatively, the variable chains may be linked by an intermolecular disulfide bond or cross-linked by chemicals such as glutaraldehyde. See Sandhu, 1992, Crit. Rev. Biotech., 12:437.

Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains, connected by an oligonucleotides linker sequence. The structural gene is inserted into an expression vector that is subsequently introduced into a host cell, such as E. coli. The recombinant host cells synthesize a single polypeptide chain with a linker peptide bridging the two V domains. Methods for producing sFv's are well-known in the art. See Whitlow et al., 1991, Methods: A Companion to Methods in Enzymology 2:97; Bird et al., 1988, Science, 242:423; U.S. Pat. No. 4,946,778; Pack et al., 1993, Bio/Technology, 11:1271, and Sandhu, 1992, Crit. Rev. Biotech., 12:437.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See Larrick et al., 1991, Methods: A Companion to Methods in Enzymology 2:106; Ritter et al. (eds.), 1995, MONOCLONAL ANTIBODIES: PRODUCTION, ENGINEERING AND CLINICAL APPLICATION, pages 166-179 (Cambridge University Press); Birch et al., (eds.), 1995, MONOCLONAL ANTIBODIES: PRINCIPLES AND APPLICATIONS, pages 137-185 (Wiley-Liss, Inc.). Where an antibody-secreting hybridoma cell line is publicly available, the CDR sequences encoding antigen-binding specificity may be obtained, incorporated into chimeric or humanized antibodies, and used.

Chimeric and Humanized Antibodies

A chimeric antibody is a recombinant protein in which the variable regions of a human antibody have been replaced by the variable regions of, for example, a mouse antibody, including the complementarity-determining regions (CDRs) of the mouse antibody. Chimeric antibodies exhibit decreased immunogenicity and increased stability when administered to a subject. Methods for constructing chimeric antibodies are well known in the art (e.g., Leung et al., 1994, Hybridoma 13:469).

A chimeric monoclonal antibody may be humanized by transferring the mouse CDRs from the heavy and light variable chains of the mouse immunoglobulin into the corresponding variable domains of a human antibody. The mouse framework regions (FR) in the chimeric monoclonal antibody are also replaced with human FR sequences. To preserve the stability and antigen specificity of the humanized monoclonal, one or more human FR residues may be replaced by the mouse counterpart residues. Humanized monoclonal antibodies may be used for therapeutic treatment of subjects. The affinity of humanized antibodies for a target may also be increased by selected modification of the CDR sequences (WO0029584A1). Techniques for production of humanized monoclonal antibodies are well known in the art. (See, e.g., Jones et al., 1986, Nature, 321:522; Riechmann et al., Nature, 1988, 332:323; Verhoeyen et al., 1988, Science, 239:1534; Carter et al., 1992, Proc. Nat'l Acad. Sci. USA, 89:4285; Sandhu, Crit. Rev. Biotech., 1992, 12:437; Tempest et al., 1991, Biotechnology 9:266; Singer et al., J. Immunol., 1993, 150:2844.)

Other embodiments may concern non-human primate antibodies. General techniques for raising therapeutically useful antibodies in baboons may be found, for example, in Goldenberg et al., WO 91/11465 (1991), and in Losman et al., Int. J. Cancer 46: 310 (1990).

Human Antibodies

Methods for producing fully human antibodies using either combinatorial approaches or transgenic animals transformed with human immunoglobulin loci are known in the art (e.g., Mancini et al., 2004, New Microbiol. 27:315-28; Conrad and Scheller, 2005, Comb. Chem. High Throughput Screen. 8:117-26; Brekke and Loset, 2003, Curr. Opin. Phamacol. 3:544-50; each incorporated herein by reference). Such fully human antibodies are expected to exhibit even fewer side effects than chimeric or humanized antibodies and to function in vivo as essentially endogenous human antibodies. In certain embodiments, the claimed methods and procedures may utilize human antibodies produced by such techniques.

In one alternative, the phage display technique may be used to generate human antibodies (e.g., Dantas-Barbosa et al., 2005, *Genet. Mol. Res.* 4:126-40, incorporated herein by reference). Human antibodies may be generated from normal humans or from humans that exhibit a particular disease state, such as cancer (Dantas-Barbosa et al., 2005). The advantage to constructing human antibodies from a diseased individual is that the circulating antibody repertoire may be biased towards antibodies against disease-associated antigens.

In one non-limiting example of this methodology, Dantas-Barbosa et al. (2005) constructed a phage display library of human Fab antibody fragments from osteosarcoma patients. Generally, total RNA was obtained from circulating blood lymphocytes (Id.). Recombinant Fab were cloned from the µ, γ and κ chain antibody repertoires and inserted into a phage display library (Id.). RNAs were converted to cDNAs and used to make Fab cDNA libraries using specific primers against the heavy and light chain immunoglobulin sequences (Marks et al., 1991, *J. Mol. Biol.* 222:581-97, incorporated herein by reference). Library construction was performed according to Andris-Widhopf et al. (2000, In: *Phage Display Laboratory Manual*, Barbas et al. (eds), 1st edition, Cold Spring Harbor Laboratory Press, Cold Spring Harbor, N.Y. pp. 9.1 to 9.22, incorporated herein by reference). The final Fab fragments were digested with restriction endonucleases and inserted into the bacteriophage genome to make the phage display library. Such libraries may be screened by standard phage display methods, as known in the art. The skilled artisan will realize that this technique is exemplary only and any known method for making and screening human antibodies or antibody fragments by phage display may be utilized.

In another alternative, transgenic animals that have been genetically engineered to produce human antibodies may be used to generate antibodies against essentially any immunogenic target, using standard immunization protocols. A non-limiting example of such a system is the XenoMouse® (e.g., Green et al., 1999, *J. Immunol. Methods* 231:11-23, incorporated herein by reference) from Abgenix (Fremont, Calif.). In the XenoMouse® and similar animals, the mouse antibody genes have been inactivated and replaced by functional human antibody genes, while the remainder of the mouse immune system remains intact.

The XenoMouse® was transformed with germline-configured YACs (yeast artificial chromosomes) that contained portions of the human IgH and Igkappa loci, including the majority of the variable region sequences, along accessory genes and regulatory sequences. The human variable region repertoire may be used to generate antibody producing B cells, which may be processed into hybridomas by known techniques. A XenoMouse® immunized with a target antigen will produce human antibodies by the normal immune response, which may be harvested and/or produced by standard techniques discussed above. A variety of strains of XenoMouse® are available, each of which is capable of producing a different class of antibody. Such human antibodies may be coupled to other molecules by chemical cross-linking or other known methodologies. Transgenically produced human antibodies have been shown to have therapeutic potential, while retaining the pharmacokinetic properties of normal human antibodies (Green et al., 1999). The skilled artisan will realize that the claimed compositions and methods are not limited to use of the XenoMouse® system but may utilize any transgenic animal that has been genetically engineered to produce human antibodies.

Pre-Targeting

One strategy for use of bi-specific bioactive assemblies includes pre-targeting methodologies, in which an effector molecule is administered to a subject after a bi-specific assembly has been administered. The bi-specific assembly, which would include a binding site for an effector, hapten or carrier and one for the diseased tissue, localizes to the diseased tissue and increases the specificity of localization of the effector to the diseased tissue (U.S. Patent Application No. 20050002945). Because the effector molecule may be cleared from circulation much more rapidly than the bi-specific assembly, normal tissues may have a decreased exposure to the effector molecule when a pre-targeting strategy is used than when the effector molecule is directly linked to the disease targeting antibody.

Pre-targeting methods have been developed to increase the target:background ratios of detection or therapeutic agents. Examples of pre-targeting and biotin/avidin approaches are described, for example, in Goodwin et al., U.S. Pat. No. 4,863,713; Goodwin et al., J. Nucl. Med. 29:226, 1988; Hnatowich et al., J. Nucl. Med. 28:1294, 1987; Oehr et al., J. Nucl. Med. 29:728, 1988; Klibanov et al., J. Nucl. Med. 29:1951, 1988; Sinitsyn et al., J. Nucl. Med. 30:66, 1989; Kalofonos et al., J. Nucl. Med. 31:1791, 1990; Schechter et al., Int. J. Cancer 48:167, 1991; Paganelli et al., Cancer Res. 51:5960, 1991; Paganelli et al., Nucl. Med. Commun. 12:211, 1991; U.S. Pat. No. 5,256,395; Stickney et al., Cancer Res. 51:6650, 1991; Yuan et al., Cancer Res. 51:3119, 1991; U.S. Pat. No. 6,077,499; U.S. Ser. No. 09/597,580; U.S. Ser. No. 10/361,026; U.S. Ser. No. 09/337,756; U.S. Ser. No. 09/823,746; U.S. Ser. No. 10/116,116; U.S. Ser. No. 09/382,186; U.S. Ser. No. 10/150,654; U.S. Pat. No. 6,090,381; U.S. Pat. No. 6,472,511; U.S. Ser. No. 10/114,315; U.S. Provisional Application No. 60/386,411; U.S. Provisional Application No. 60/345,641; U.S. Provisional Application No. 60/3328,835; U.S. Provisional Application No. 60/426,379; U.S. Ser. No. 09/823,746; U.S. Ser. No. 09/337,756; and U.S. Provisional Application No. 60/342,103, all of which are incorporated herein by reference.

In certain embodiments, bi-specific assemblies and targetable constructs may be of use in treating and/or imaging normal or diseased tissue and organs, for example using the methods described in U.S. Pat. Nos. 6,126,916; 6,077,499; 6,010,680; 5,776,095; 5,776,094; 5,776,093; 5,772,981; 5,753,206; 5,746,996; 5,697,902; 5,328,679; 5,128,119; 5,101,827; and 4,735,210, each incorporated herein by reference. Additional methods are described in U.S. application Ser. No. 09/337,756 filed Jun. 22, 1999 and in U.S. application Ser. No. 09/823,746, filed Apr. 3, 2001.

Aptamers

In certain embodiments, a precursor for bioactive assembly formation may comprise an aptamer. Methods of constructing and determining the binding characteristics of aptamers are well known in the art. For example, such techniques are described in U.S. Pat. Nos. 5,582,981, 5,595,877 and 5,637,459, each incorporated herein by reference.

Aptamers may be prepared by any known method, including synthetic, recombinant, and purification methods, and may be used alone or in combination with other ligands specific for the same target. In general, a minimum of approximately 3 nucleotides, preferably at least 5 nucleotides, are necessary to effect specific binding. Aptamers of sequences shorter than 10 bases may be feasible, although aptamers of 10, 20, 30 or 40 nucleotides may be preferred.

Aptamers need to contain the sequence that confers binding specificity, but may be extended with flanking regions and otherwise derivatized. In preferred embodiments, the binding sequences of aptamers may be flanked by primer-binding sequences, facilitating the amplification of the aptamers by PCR or other amplification techniques. In a further embodiment, the flanking sequence may comprise a specific sequence that preferentially recognizes or binds a moiety to enhance the immobilization of the aptamer to a substrate.

Aptamers may be isolated, sequenced, and/or amplified or synthesized as conventional DNA or RNA molecules. Alternatively, aptamers of interest may comprise modified oligomers. Any of the hydroxyl groups ordinarily present in aptamers may be replaced by phosphonate groups, phosphate groups, protected by a standard protecting group, or activated to prepare additional linkages to other nucleotides, or may be conjugated to solid supports. One or more phosphodiester linkages may be replaced by alternative linking groups, such as P(O)O replaced by P(O)S, P(O)NR$_2$, P(O)R, P(O)OR', CO, or CNR$_2$, wherein R is H or alkyl (1-20C) and R' is alkyl (1-20C); in addition, this group may be attached to adjacent nucleotides through O or S, Not all linkages in an oligomer need to be identical.

Methods for preparation and screening of aptamers that bind to particular targets of interest are well known, for example U.S. Pat. No. 5,475,096 and U.S. Pat. No. 5,270,163, each incorporated by reference. The technique generally involves selection from a mixture of candidate aptamers and step-wise iterations of binding, separation of bound from unbound aptamers and amplification. Because only a small number of sequences (possibly only one molecule of aptamer) corresponding to the highest affinity aptamers exist in the mixture, it is generally desirable to set the partitioning criteria so that a significant amount of aptamers in the mixture (approximately 5-50%) is retained during separation. Each cycle results in an enrichment of aptamers with high affinity for the target. Repetition for between three to six selection and amplification cycles may be used to generate aptamers that bind with high affinity and specificity to the target.

Avimers

In certain embodiments, the peripheral modules and/or assemblies described herein may comprise one or more avimer sequences. Avimers are a class of binding proteins somewhat similar to antibodies in their affinities and specificities for various target molecules. They were developed from human extracellular receptor domains by in vitro exon shuffling and phage display. (Silverman et al., 2005, Nat. Biotechnol. 23:1493-94; Silverman et al., 2006, Nat. Biotechnol. 24:220.) The resulting multidomain proteins may comprise multiple independent binding domains that may exhibit improved affinity (in some cases sub-nanomolar) and specificity compared with single-epitope binding proteins. (Id.) In various embodiments, avimers may be attached to, for example, DDD and/or AD sequences for use in the claimed methods and compositions. Additional details concerning methods of construction and use of avimers are disclosed, for example, in U.S. Patent Application Publication Nos. 20040175756, 20050048512, 20050053973, 20050089932 and 20050221384, the Examples section of each of which is incorporated herein by reference.

Methods of Disease Tissue Detection, Diagnosis and Imaging
Protein-Based In Vitro Diagnosis The present invention contemplates the use of bioactive assemblies to screen biological samples in vitro and/or in vivo for the presence of the disease-associated antigens. In exemplary immunoassays, a bioactive assembly comprising an antibody, fusion protein, or fragment thereof may be utilized in liquid phase or bound to a solid-phase carrier, as described below. In preferred embodiments, particularly those involving in vivo administration, the antibody or fragment thereof is humanized. Also preferred, the antibody or fragment thereof is fully human. Still more preferred, the fusion protein comprises a humanized or fully human antibody. The skilled artisan will realize that a wide variety of techniques are known for determining levels of expression of a particular gene and any such known method, such as immunoassay, RT-PCR, mRNA purification and/or cDNA preparation followed by hybridization to a gene expression assay chip may be utilized to determine levels of expression in individual subjects and/or tissues. Exemplary in vitro assays of use include RIA, ELISA, sandwich ELISA, Western blot, slot blot, dot blot, and the like. Although such techniques were developed using intact antibodies, bioactive assemblies that incorporate antibodies, antibody fragments or other binding moieties may be used.

Bioactive assemblies incorporating antibodies, fusion proteins, antibody fragments and/or other binding moieties may also be used to detect the presence of a target antigen in tissue sections prepared from a histological specimen. Such in situ detection can be used to determine the presence of the antigen and to determine the distribution of the antigen in the examined tissue. In situ detection can be accomplished by applying a detectably-labeled assembly to frozen or paraffin-embedded tissue sections. General techniques of in situ detection are well-known to those of ordinary skill. See, for example, Ponder, "Cell Marking Techniques and Their Application," in MAMMALIAN DEVELOPMENT: A PRACTICAL APPROACH 113-38 Monk (ed.) (IRL Press 1987), and Coligan at pages 5.8.1-5.8.8.

Bioactive assemblies can be detectably labeled with any appropriate marker moiety, for example, a radioisotope, an enzyme, a fluorescent label, a dye, a chromogen, a chemiluminescent label, a bioluminescent label or a paramagnetic label.

The marker moiety may be a radioisotope that is detected by such means as the use of a gamma counter or a beta-scintillation counter or by autoradiography. In a preferred embodiment, the diagnostic conjugate is a gamma-, beta- or a positron-emitting isotope. A marker moiety refers to a molecule that will generate a signal under predetermined conditions. Examples of marker moieties include radioisotopes, enzymes, fluorescent labels, chemiluminescent labels, bioluminescent labels and paramagnetic labels. The binding of marker moieties to bioactive assemblies can be accomplished using standard techniques known to the art. Typical methodology in this regard is described by Kennedy et al., Clin. Chim. Acta 70:1 (1976), Schurs et al., Clin. Chim. Acta 81: 1 (1977), Shih et al., Int'l J. Cancer 46: 1101 (1990).

In Vivo Diagnosis

Methods of diagnostic imaging with labeled peptides or MAbs are well-known. For example, in the technique of immunoscintigraphy, ligands or antibodies are labeled with a gamma-emitting radioisotope and introduced into a patient. A gamma camera is used to detect the location and distribution of gamma-emitting radioisotopes. See, for example, Srivastava (ed.), RADIOLABELED MONOCLONAL ANTIBODIES FOR IMAGING AND THERAPY (Plenum Press 1988), Chase, "Medical Applications of Radioisotopes," in REMINGTON'S PHARMACEUTICAL SCIENCES, 18th Edition, Gennaro et al. (eds.), pp. 624-652 (Mack Publishing Co., 1990), and Brown, "Clinical Use of Monoclonal Antibodies," in BIOTECHNOLOGY AND PHARMACY 227-49, Pezzuto et al. (eds.) (Chapman & Hall 1993). Also preferred is the use of positron-emitting radionuclides (PET isotopes), such as with an energy of 511 keV, such as $^{18}F$, $^{68}Ga$, $^{64}Cu$, and $^{124}I$. Such imaging can be conducted by direct labeling of the bioactive assembly, or by a pretargeted imaging method, as described in Goldenberg et al, "Antibody Pre-targeting Advances Cancer Radioimmunodetection and Radioimmunotherapy," (J Clin Oncol 2006; 24:823-834), see also U.S. Patent Publication Nos. 20050002945, 20040018557, 20030148409 and 20050014207, each incorporated herein by reference.

The radiation dose delivered to the patient is maintained at as low a level as possible through the choice of isotope for the best combination of minimum half-life, minimum retention in the body, and minimum quantity of isotope which will permit detection and accurate measurement. Examples of radioisotopes that are appropriate for diagnostic imaging include $^{99m}$Tc and $^{111}$In.

The bioactive assemblies, or haptens or carriers that bind to them, also can be labeled with paramagnetic ions and a variety of radiological contrast agents for purposes of in vivo diagnosis. Contrast agents that are particularly useful for magnetic resonance imaging comprise gadolinium, manganese, dysprosium, lanthanum, or iron ions. Additional agents include chromium, copper, cobalt, nickel, rhenium, europium, terbium, holmium, or neodymium. ligands, antibodies and fragments thereof can also be conjugated to ultrasound contrast/enhancing agents. For example, one ultrasound contrast agent is a liposome that comprises a humanized IgG or fragment thereof. Also preferred, the ultrasound contrast agent is a liposome that is gas filled.

Imaging Agents and Radioisotopes

Many appropriate imaging agents are known in the art, as are methods for their attachment to proteins or peptides (see, e.g., U.S. Pat. Nos. 5,021,236 and 4,472,509, both incorporated herein by reference). Certain attachment methods involve the use of a metal chelate complex employing, for example, an organic chelating agent such a DTPA attached to the protein or peptide (U.S. Pat. No. 4,472,509). Proteins or peptides also may be reacted with an enzyme in the presence of a coupling agent such as glutaraldehyde or periodate. Conjugates with fluorescein markers are prepared in the presence of these coupling agents or by reaction with an isothiocyanate.

Non-limiting examples of paramagnetic ions of potential use as imaging agents include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III), with gadolinium being particularly preferred. Ions useful in other contexts, such as X-ray imaging, include but are not limited to lanthanum (III), gold (III), lead (II), and especially bismuth (III).

Radioisotopes of potential use as imaging or therapeutic agents include astatine$^{211}$, carbon$^{14}$, chromium$^{51}$, chlorine$^{36}$, cobalt$^{57}$, cobalt$^{58}$, copper$^{62}$, copper$^{64}$, copper$^{67}$, Eu$^{152}$, fluorine$^{18}$, gallium$^{67}$, gallium$^{68}$, hydrogen$^{3}$, iodine$^{123}$, iodine$^{124}$, iodine$^{125}$, iodine$^{131}$, indium$^{111}$, iron$^{52}$, iron$^{59}$, lutetium$^{177}$, phosphorus$^{32}$, phosphorus$^{33}$, rhenium$^{186}$, rhenium$^{188}$, Sc$^{47}$, selenium$^{75}$, silver$^{111}$, sulphur$^{35}$, technetium$^{94m}$, technetium$^{99m}$, yttrium$^{86}$ and yttrium$^{90}$, and zirconium$^{89}$. I$^{125}$ is often being preferred for use in certain embodiments, and technetium$^{99m}$ and indium$^{111}$ are also often preferred due to their low energy and suitability for long-range detection.

Radioactively labeled proteins or peptides may be produced according to well-known methods in the art. For instance, they can be iodinated by contact with sodium or potassium iodide and a chemical oxidizing agent such as sodium hypochlorite, or an enzymatic oxidizing agent, such as lactoperoxidase. Proteins or peptides may be labeled with technetium-$^{99m}$ by ligand exchange process, for example, by reducing pertechnate with stannous solution, chelating the reduced technetium onto a Sephadex column and applying the peptide to this column or by direct labeling techniques, e.g., by incubating pertechnate, a reducing agent such as SNCl$_2$, a buffer solution such as sodium-potassium phthalate solution, and the peptide. Intermediary functional groups which are often used to bind radioisotopes which exist as metallic ions to peptides include diethylenetriaminepentaacetic acid (DTPA), DOTA, NOTA, porphyrin chelators and ethylene diaminetetracetic acid (EDTA). Also contemplated for use are fluorescent labels, including rhodamine, fluorescein isothiocyanate and renographin.

In certain embodiments, the proteins or peptides may be linked to a secondary binding ligand or to an enzyme (an enzyme tag) that will generate a colored product upon contact with a chromogenic substrate. Examples of suitable enzymes include urease, alkaline phosphatase, (horseradish) hydrogen peroxidase and glucose oxidase. Preferred secondary binding ligands are biotin and avidin or streptavidin compounds. The use of such labels is well known to those of skill in the art in light and is described, for example, in U.S. Pat. Nos. 3,817,837; 3,850,752; 3,939,350; 3,996,345; 4,277,437; 4,275,149 and 4,366,241; each incorporated herein by reference. These fluorescent labels are preferred for in vitro uses, but may also be of utility in in vivo applications, particularly endoscopic or intravascular detection procedures.

In alternative embodiments, ligands, antibodies, or other proteins or peptides may be tagged with a fluorescent marker. Non-limiting examples of photodetectable labels include Alexa 350, Alexa 430, AMCA, aminoacridine, BODIPY 630/650, BODIPY 650/665, BODIPY-FL, BODIPY-R6G, BODIPY-TMR, BODIPY-TR, 5-carboxy-4',5'-dichloro-2', 7'-dimethoxy fluorescein, 5-carboxy-2',4',5',7'-tetrachlorofluorescein, 5-carboxyfluorescein, 5-carboxyrhodamine, 6-carboxyrhodamine, 6-carboxytetramethyl amino, Cascade Blue, Cy2, Cy3, Cy5,6-FAM, dansyl chloride, Fluorescein, HEX, 6-JOE, NBD (7-nitrobenz-2-oxa-1,3-diazole), Oregon Green 488, Oregon Green 500, Oregon Green 514, Pacific Blue, phthalic acid, terephthalic acid, isophthalic acid, cresyl fast violet, cresyl blue violet, brilliant cresyl blue, para-aminobenzoic acid, erythrosine, phthalocyanines, azomethines, cyanines, xanthines, succinylfluoresceins, rare earth metal cryptates, europium trisbipyridine diamine, a europium cryptate or chelate, diamine, dicyanins, La Jolla blue dye, allopycocyanin, allocoyanin B, phycocyanin C, phycocyanin R, thiamine, phycoerythrocyanin, phycoerythrin R, REG, Rhodamine Green, rhodamine isothiocyanate, Rhodamine Red, ROX, TAMRA, TET, TRIT (tetramethyl rhodamine isothiol), Tetramethylrhodamine, Edans and Texas Red. These and other luminescent labels may be obtained from commercial sources such as Molecular Probes (Eugene, Oreg.), and EMD Biosciences (San Diego, Calif.).

Chemiluminescent labeling compounds of use may include luminol, isoluminol, an aromatic acridinium ester, an imidazole, an acridinium salt and an oxalate ester, or a bioluminescent compound such as luciferin, luciferase and aequorin. Diagnostic conjugates may be used, for example, in intraoperative, endoscopic, or intravascular tumor or disease diagnosis.

In various embodiments, labels of use may comprise metal nanoparticles. Methods of preparing nanoparticles are known. (See e.g., U.S. Pat. Nos. 6,054,495; 6,127,120; 6,149,868; Lee and Meisel, *J. Phys. Chem.* 86:3391-3395, 1982.) Nanoparticles may also be obtained from commercial sources (e.g., Nanoprobes Inc., Yaphank, N.Y.; Polysciences, Inc., Warrington, Pa.). Modified nanoparticles are available commercially, such as Nanogold® nanoparticles from Nanoprobes, Inc. (Yaphank, N.Y.). Functionalized nanoparticles of use for conjugation to proteins or peptides may be commercially obtained.

Therapeutic Agents

Pharmaceutical Compositions

In some embodiments, a bioactive assembly and/or one or more other therapeutic agents may be administered to a subject, such as a subject with cancer. Such agents may be administered in the form of pharmaceutical compositions. Generally, this will entail preparing compositions that are essentially free of impurities that could be harmful to humans or animals. One skilled in the art would know that a pharmaceutical composition can be administered to a subject by various routes including, for example, orally or parenterally, such as intravenously.

In certain embodiments, an effective amount of a therapeutic agent must be administered to the subject. An "effective amount" is the amount of the agent that produces a desired effect. An effective amount will depend, for example, on the efficacy of the agent and on the intended effect. For example, a lesser amount of an antiangiogenic agent may be required for treatment of a hyperplastic condition, such as macular degeneration or endometriosis, compared to the amount required for cancer therapy in order to reduce or eliminate a solid tumor, or to prevent or reduce its metastasizing. An effective amount of a particular agent for a specific purpose can be determined using methods well known to those in the art.

Chemotherapeutic Agents

In certain embodiments, chemotherapeutic agents may be administered. Anti-cancer chemotherapeutic agents of use include, but are not limited to, 5-fluorouracil, bleomycin, busulfan, camptothecins, carboplatin, chlorambucil, cisplatin (CDDP), cyclophosphamide, dactinomycin, daunorubicin, doxorubicin, estrogen receptor binding agents, etoposide (VP16), farnesyl-protein transferase inhibitors, gemcitabine, ifosfamide, mechlorethamine, melphalan, methotrexate, mitomycin, navelbine, nitrosurea, plicomycin, procarbazine, raloxifene, tamoxifen, taxol, temazolomide (an aqueous form of DTIC), transplatinum, vinblastine and methotrexate, vincristine, or any analog or derivative variant of the foregoing. Chemotherapeutic agents of use against infectious organisms include, but are not limited to, acyclovir, albendazole, amantadine, amikacin, amoxicillin, amphotericin B, ampicillin, aztreonam, azithromycin, bacitracin, bactrim, Batrafen®, bifonazole, carbenicillin, caspofungin, cefaclor, cefazolin, cephalosporins, cefepime, ceftriaxone, cefotaxime, chloramphenicol, cidofovir, Cipro®, clarithromycin, clavulanic acid, clotrimazole, cloxacillin, doxycycline, econazole, erythrocycline, erythromycin, flagyl, fluconazole, flucytosine, foscamet, furazolidone, ganciclovir, gentamycin, imipenem, isoniazid, itraconazole, kanamycin, ketoconazole, lincomycin, linezolid, meropenem, miconazole, minocycline, naftifine, nalidixic acid, neomycin, netilmicin, nitrofurantoin, nystatin, oseltamivir, oxacillin, paromomycin, penicillin, pentamidine, piperacillin-tazobactam, rifabutin, rifampin, rimantadine, streptomycin, sulfamethoxazole, sulfasalazine, tetracycline, tioconazole, tobramycin, tolciclate, tolnaftate, trimethoprim sulfamethoxazole, valacyclovir, vancomycin, zanamir, and zithromycin.

Chemotherapeutic agents and methods of administration, dosages, etc., are well known to those of skill in the art (see for example, the "Physicians Desk Reference", Goodman & Gilman's "The Pharmacological Basis of Therapeutics" and in "Remington's Pharmaceutical Sciences", incorporated herein by reference in relevant parts). Some variation in dosage will necessarily occur depending on the condition of the subject being treated. The person responsible for administration will, in any event, determine the appropriate dose for the individual subject.

Hormones

Corticosteroid hormones can increase the effectiveness of other chemotherapy agents, and consequently, they are frequently used in combination treatments. Prednisone and dexamethasone are examples of corticosteroid hormones. Progestins, such as hydroxyprogesterone caproate, medroxyprogesterone acetate, and megestrol acetate, have been used in cancers of the endometrium and breast. Estrogens such as diethylstilbestrol and ethinyl estradiol have been used in cancers such as prostate cancer. Antiestrogens such as tamoxifen have been used in cancers such as breast cancer. Androgens such as testosterone propionate and fluoxymesterone have also been used in treating breast cancer.

Angiogenesis Inhibitors

In certain embodiments, anti-angiogenic agents, such as angiostatin, baculostatin, canstatin, maspin, anti-VEGF antibodies, anti-P1GF peptides and antibodies, anti-vascular growth factor antibodies, anti-Flk-1 antibodies, anti-Flt-1 antibodies and peptides, laminin peptides, fibronectin peptides, plasminogen activator inhibitors, tissue metalloproteinase inhibitors, interferons, interleukin-12, IP-10, Gro-$\beta$, thrombospondin, 2-methoxyoestradiol, proliferin-related protein, carboxiamidotriazole, CM101, Marimastat, pentosan polysulphate, angiopoietin-2, interferon-alpha, herbimycin A, PNU145156E, 16K prolactin fragment, Linomide, thalidomide, pentoxifylline, genistein, TNP-470, endostatin, paclitaxel, accutin, angiostatin, cidofovir, vincristine, bleomycin, AGM-1470, platelet factor 4 or minocycline may be of use.

Immunomodulators

As used herein, the term "immunomodulator" includes cytokines, stem cell growth factors, lymphotoxins and hematopoietic factors, such as interleukins, colony-stimulating factors, interferons (e.g., interferons-$\alpha$, -$\beta$ and -$\gamma$) and the stem cell growth factor designated "S1 factor." Examples of suitable immunomodulator moieties include IL-2, IL-6, IL-10, IL-12, IL-18, IL-21, interferon-gamma, TNF-alpha, and the like.

The term "cytokine" is a generic term for proteins or peptides released by one cell population which act on another cell as intercellular mediators. As used broadly herein, examples of cytokines include lymphokines, monokines, growth factors and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; prostaglandin, fibroblast growth factor; prolactin; placental lactogen, OB protein; tumor necrosis factor-$\alpha$ and -$\beta$; mullerian-inhibiting substance; mouse gonadotropin-associated peptide; inhibin; activin; vascular endothelial growth factor; integrin; thrombopoietin (TPO); nerve growth factors such as NGF-$\beta$; platelet-growth factor; transforming growth factors (TGFs) such as TGF-$\alpha$ and TGF-$\beta$; insulin-like growth factor-I and -II; erythropoietin (EPO); osteoinductive factors; interferons such as interferon-$\alpha$, -$\beta$, and -$\gamma$; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1a, IL-2, IL-3, IL-4, IL-5, IL-6, IL-7, IL-8, IL-9, IL-10, IL-11, IL-12; IL-13, IL-14, IL-15, IL-16, IL-17, IL-18, IL-21, LIF, G-CSF, GM-CSF, M-CSF, EPO, kit-ligand or FLT-3, angiostatin, thrombospondin, endostatin, tumor necrosis factor and LT. As used herein, the term cytokine includes proteins from natural sources or from recombinant cell culture and biologically active equivalents of the native sequence cytokines.

Chemokines generally act as chemoattractants to recruit immune effector cells to the site of chemokine expression. Chemokines include, but are not limited to, RANTES, MCAF, MIP1-alpha, MIP1-Beta, and IP-10. The skilled artisan will recognize that certain cytokines are also known to have chemoattractant effects and could also be classified under the term chemokines. Similarly, the terms immunomodulator and cytokine overlap in their respective members.

Radioisotope Therapy and Radioimmunotherapy

In some embodiments, the peptides and/or proteins may be of use in radionuclide therapy or radioimmunotherapy methods (see, e.g., Govindan et al., 2005, *Technology in Cancer Research & Treatment*, 4:375-91; Sharkey and Goldenberg, 2005, *J. Nucl. Med.* 46:115 S-127S; Goldenberg et al. (J Clin Oncol 2006; 24:823-834), "Antibody Pre-targeting Advances Cancer Radioimmunodetection and Radioimmunotherapy," each incorporated herein by reference.) In specific embodiments, bioactive assemblies may be directly tagged with a radioisotope of use and administered to a subject. In alternative embodiments, radioisotope(s) may be administered in a pre-targeting method as discussed above, using a haptenic peptide or ligand that is radiolabeled and injected after administration of a bispecific bioactive assembly that localizes at the site of elevated expression in the diseased tissue.

Radioactive isotopes useful for treating diseased tissue include, but are not limited to—$^{111}$In, $^{177}$Lu, $^{212}$Bi, $^{213}$Bi, $^{211}$At, $^{62}$Cu, $^{67}$Cu, $^{90}$Y, $^{125}$I, $^{131}$I, $^{32}$P, $^{33}$P, $^{47}$SC, $^{111}$Ag, $^{67}$Ga, $^{142}$Pr, $^{153}$Sm, $^{161}$Tb, $^{166}$Dy, $^{166}$Ho, $^{186}$Re, $^{188}$Re, $^{189}$Re, $^{212}$Ra, $^{225}$Ac, $^{59}$Fe, $^{75}$Se, $^{77}$As, $^{89}$Sr, $^{99}$Mo, $^{105}$Rh, $^{109}$Pd, $^{143}$Pr, $^{149}$Pm, $^{169}$Er, $^{194}$Ir, $^{198}$Au, $^{199}$Au, and $^{211}$Pb. The therapeutic radionuclide preferably has a decay energy in the range of 20 to 6,000 keV, preferably in the ranges 60 to 200 keV for an Auger emitter, 100-2,500 keV for a beta emitter, and 4,000-6,000 keV for an alpha emitter. Maximum decay energies of useful beta-particle-emitting nuclides are preferably 20-5,000 keV, more preferably 100-4,000 keV, and most preferably 500-2,500 keV. Also preferred are radionuclides that substantially decay with Auger-emitting particles. For example, Co-58, Ga-67, Br-80m, Tc-99m, Rh-103m, Pt-109, In-111, Sb-119, I-125, Ho-161, Os-189m and Ir-192. Decay energies of useful beta-particle-emitting nuclides are preferably <1,000 keV, more preferably <100 keV, and most preferably <70 keV. Also preferred are radionuclides that substantially decay with generation of alpha-particles. Such radionuclides include, but are not limited to: Dy-152, At-211, Bi-212, Ra-223, Rn-219, Po-215, Bi-211, Ac-225, Fr-221, At-217, Bi-213 and Fm-255. Decay energies of useful alpha-particle-emitting radionuclides are preferably 2,000-10,000 keV, more preferably 3,000-8,000 keV, and most preferably 4,000-7,000 keV.

For example, $^{67}$Cu, considered one of the more promising radioisotopes for radioimmunotherapy due to its 61.5 hour half-life and abundant supply of beta particles and gamma rays, can be conjugated to a protein or peptide using the chelating agent, p-bromoacetamido-benzyl-tetraethylamine-tetraacetic acid (TETA). Alternatively, $^{90}$Y, which emits an energetic beta particle, can be coupled to a peptide, antibody, fusion protein, or fragment thereof, using diethylenetriaminepentaacetic acid (DTPA).

Additional potential radioisotopes include $^{11}$C, $^{13}$N, $^{15}$O, $^{75}$Br, $^{198}$Au, $^{224}$Ac, $^{126}$I, $^{133}$I, $^{77}$Br, $^{113m}$In, $^{95}$Ru, $^{97}$Ru, $^{103}$Ru, $^{105}$Ru, $^{107}$Hg, $^{203}$Hg, $^{121m}$Te, $^{122m}$Te, $^{125m}$Te, $^{165}$Tm, $^{167}$Tm, $^{168}$Tm, $^{197}$Pt, $^{109}$Pd, $^{105}$Rh, $^{142}$Pr, $^{143}$Pr, $^{161}$Tb, $^{166}$Ho, $^{199}$Au, $^{57}$Co, $^{58}$Co, $^{51}$Cr, $^{59}$Fe, $^{71}$Se, $^{201}$Tl, $^{225}$Ac, $^{76}$Br, $^{169}$Yb, and the like.

In another embodiment, a radiosensitizer can be used. The addition of the radiosensitizer can result in enhanced efficacy. Radiosensitizers are described in D. M. Goldenberg (ed.), CANCER THERAPY WITH RADIOLABELED ANTIBODIES, CRC Press (1995), which is incorporated herein by reference in its entirety.

The peptide, antibody, antibody fragment, or fusion protein that has a boron addend-loaded carrier for thermal neutron activation therapy will normally be effected in similar ways. However, it will be advantageous to wait until non-targeted immunoconjugate clears before neutron irradiation is performed. Clearance can be accelerated using an antibody that binds to the ligand. See U.S. Pat. No. 4,624,846 for a description of this general principle. For example, boron addends such as carboranes, can be attached to antibodies. Carboranes can be prepared with carboxyl functions on pendant side chains, as is well-known in the art. Attachment of carboranes to a carrier, such as aminodextran, can be achieved by activation of the carboxyl groups of the carboranes and condensation with amines on the carrier. The intermediate conjugate is then conjugated to the antibody. After administration of the conjugate, a boron addend is activated by thermal neutron irradiation and converted to radioactive atoms which decay by alpha-emission to produce highly toxic, short-range effects.

Kits

Various embodiments may concern kits containing components suitable for treating or diagnosing diseased tissue in a patient. Exemplary kits may contain at least one bioactive assembly. If the composition containing components for administration is not formulated for delivery via the alimentary canal, such as by oral delivery, a device capable of delivering the kit components through some other route may be included. One type of device, for applications such as parenteral delivery, is a syringe that is used to inject the composition into the body of a subject. Inhalation devices may also be used.

The kit components may be packaged together or separated into two or more separate containers. In some embodiments, the containers may be vials that contain sterile, lyophilized formulations of a composition that are suitable for reconstitution. A kit may also contain one or more buffers suitable for reconstitution and/or dilution of other reagents. Other containers that may be used include, but are not limited to, a pouch, tray, box, tube, or the like. Kit components may be packaged and maintained sterilely within the containers. Another component that can be included is instructions to a person using a kit for its use.

EXAMPLES

The following examples are provided to illustrate, but not to limit the claims of the present invention.

Example 1

Generation of a Fusion Protein Comprising a Heat Shock Protein, AD2 and AD3 (Type-A Adaptor Module) and Use A fusion protein in which AD2 and AD3 are linked, respectively, to the amino and carboxyl termini of a heat shock protein such as HSP70 or gp96 can be further docked and locked with two peripheral modules, one consisting of a DDD2-linked homodimer (X$_2$) and the other consisting of a DDD3C-linked homodimer (Y$_2$) to form a complex composed of X$_2$ (Ma)Y$_2$. One choice of the two peripheral modules is the Ig-like domains 1 and 2 of human CD22 and the extracellular region of human CD20, which upon conjugation to the HSP-based adaptor module is of use as a therapeutic vaccine for B cell lymphomas. Another choice of the two peripheral modules is the N-A1 and the A3-B3 domains of CEACAM5, which upon conjugation to the HSP-based adaptor module is of use as a therapeutic vaccine for CEA-expressing cancers. The two peripheral modules can also be hLL1 Fab and the extracelluar region of HER2, which upon conjugation to the HSP-based adaptor module is of use as a therapeutic vaccine for cancers over-expressing HER2.

A vaccine comprising AD2-HSP70-AD3 stably linked to the N-A1 and the A3-B3 domains of CEACAM5 produced as described above is formulated in saline or other physiologically compatible solution and administered to patients following surgical removal of colorectal cancer. The therapeutic vaccine is given once weekly for a minimal of four weeks at a dosage in the range of 100 and 5000 μg, with the preferred dosage being about 500 μg. The route of injection is subcutaneous but the site of injection can be varied each time with the same site of injection repeated after a gap of one or more injections. For example, the first injection is given on the left thigh, the second injection on the right thigh, the third injection on the left arm, the fourth injection on the right arm, the fifth injection on the left thigh, the sixth injection on the right arm, etc. After the first cycle of four weekly injections, two more injections are given biweekly, followed by a regimen of monthly injections. The effect of the vaccine on eliciting anti-cancer immune response is evaluated by measuring (1) delayed hypersensitivity as an assessment of cellular immunity; (2) activity of cytolytic T cells in vitro; (3) levels of circulating CEA; (4) changes in tumor size using various imaging techniques such as CT scan; and (5) other biomarkers associated with CEA-expressing cancers Example 2

Treating Colorectal Cancer with a Vaccine Comprising AD2-HSP70-AD3 Stably Linked to the N-A1 and the A3-B3 Domains of CEACAM5

Patient DN is a 62-year-old male with a resected left colon carcinoma of 4 cm in diameter, diagnosed with T2N1M0 disease refused post-operative chemotherapy and is given an experimental vaccine treatment. The patient receives four weekly injections of the vaccine comprising AD2-HSP70-AD3 stably linked to the N-A1 and the A3-B3 domains of CEACAM5 in saline at a dosage of 500 μg, followed by two bi-weekly injections of the same dosage and thereafter, one monthly injection of the same dosage. The first injection is given on the left arm, the second on the right arm, the third on the right thigh, and the fourth on the left thigh. The site of the injection is then repeated. The patient is premedicated with Tylenol and antihistamines in order to mitigate any side effects.

During the injections, only grade 1 or 2 local erythema or itching at the injection sites is noted, and shortness of breadth after the fourth injection, all resolving within 4 hours. At the follow-up of 3, 6, and 12 months, which includes diagnostic imaging tests (CT and one FDG-PET study at 12 months) and serum CEA assays, no abnormalities are detected. At the 2-year follow-up, the patient is considered to be free of disease, and avoided the side effects of aggressive chemotherapy by having this experimental vaccine.

Example 3

Generation of a Polypeptide Comprising DDD2-hP1-DDD3C (Type-B Adaptor Module) and Use A polypeptide in which DDD2 and DDD3C are fused, respectively, to the amino and carboxyl termini of hP1 will self-associate into a structure composed of a homodimer of hP1 linked via disulfide bonds, which upon reduction with a thiol-containing agent is further docked and locked with two peripheral modules, one consisting of an entity derivatized with AD2 (X) and the other consisting of an entity derivatized with AD3 (Y) to form a complex composed of X(hP1)$_2$Y. Suitable choices for X and Y include receptor-targeting ligands, antibody fragments, and immunostimulatory molecules. For example, a construct of X(hP1)$_2$Y in which one of the two peripheral modules is based on anti-hTfR (human transferin receptor) Fab and the other anti-hIR (human insulin receptor) Fab can be used to carry therapeutic siRNAs or genes across the blood brain barrier (BBB) and further into glioma cells to treat brain cancers. (Zhang et al., Clin Cancer Res, 2004, 10: 3667-3677).

Example 4

Generation of a Polypeptide Comprising DDD3-hP1-AD2 (Type-C Adaptor Module) and Use A polypeptide in which DDD3 and AD2 are fused, respectively, to the amino and carboxyl termini of hP1 will self-associate into a homodimer of hP1, which can be docked and locked with two identical DDD2-linked peripheral modules (X$_2$) to form a complex composed of X$_2$(hP1)$_2$X$_2$. One area of particular promise for a construct of X$_2$(hP1)$_2$X$_2$ is to deliver nonviral vectors across the blood-brain barrier for gene therapy of brain disorders. For example, a construct of X$_2$(hP1)$_2$X$_2$ in which the peripheral module (X) is based on anti-hTfR Fab can be used to carry a DNA vector encoding the gene of tyrosine hydroxylase across the BBB for treating Parkinson's disease (Pardridge, NeuroRx®, 2005, 2: 129-138).

Example 5

Generation of a Polypeptide Comprising DDD2-CH2-CH3-DDD3C (Type-B Adaptor Module) and Use A polypeptide in which DDD2 and DDD3C are fused, respectively, to the amino and carboxyl termini of the CH2 and CH3 domains of human IgG1, will self-associate into a structure composed of two Fc subunits linked via disulfide bonds, which can be converted into a single Fc subunit upon reduction with a thiol-containing agent and further docked and locked with two peripheral modules, one consisting of an entity derivatized with AD2 (X) and the other consisting of an entity derivatized with AD3 (Y) to form a complex composed of X(Fc)Y. When the two AD-containing entities are each derived from a Fab of different specificity, the resulting assembly is an IgG-like bispecific antibody with an intact Fc.

Example 6

Generation of a Polypeptide Comprising DDD3-CH2-CH3-AD2 (Type-C Adaptor Module) and Use A polypeptide in which DDD3 and AD2 are fused, respectively, to the amino and carboxyl termini of the CH2 and CH3 domains of human IgG1, will self-associate into an Fc-containing structure, which can be docked and locked with two identical DDD2-linked peripheral modules ($X_2$) to form a complex composed of $X_2(Fc)X_2$.

Example 7

Generation of a Polypeptide Comprising DDD3C—CH2-CH3-AD2 (Type-D Adaptor Module) and Use A polypeptide in which DDD3C and AD2 are fused, respectively, to the amino and carboxyl termini of the CH2 and CH3 domains of human IgG1, will self-associate into a structure composed of two Fc subunits linked via disulfide bonds, which can be converted into a single Fc subunit upon reduction with a thiol-containing agent and docked and locked with three peripheral modules, two of which are identical DDD2-linked homodimers ($X_2$) and the third consists of an AD3-linked entity (Y), to form a complex composed of $X_2(Fc)YX_2$.

Example 8

Molecular Engineering of DDD3-CH2-CH3-AD2 and DDD3C—CH2-CH3-AD2

Two PCR reactions were performed to generate the DDD3 and DDD3C sequences using a human RIα cDNA clone (Invitrogen IMAGE clone #5531156) as a template. Both reactions used the oligonucleotide RI BglII right as the 3' PCR primer. The oligonucleotides RI BspHI Left and RI-C BspHI Left were used as 5' primers for DDD3 and DDD3C, respectively.

RI BglII Right (SEQ ID NO: 11)
5'-AGATCTGCCTTTTGCCTCCTCCTTCTC-3'

RI BspHI Left (SEQ ID NO: 12)
5'-TCATGAGCCTTCGAGAATGTGAGCTC-3'

RI-C BspHI Left (SEQ ID NO: 13)
5'-TCATGAGTTGTGGCGGAAGCCTTCGAGAATGTGAGC-3'

The Fc (CH2 and CH3 domains) was amplified using the pdHL2 vector as a template and the oligonucleotides Fc BglII Left and Fc Bam-EcoRI Right as primers.

Fc BglII Left (SEQ ID NO: 14)
5'-AGATCTGGCGCACCTGAACTCCTG-3'

Fc Bam-EcoRI Right (SEQ ID NO: 15)
5'-GAATTCGGATCCTTTACCCGGAGACAGGGAGAG-3'

Each of the amplimers was cloned in the pGemT PCR cloning vector. The Fc insert fragment was excised from pGemT with BglII and EcoRI restriction enzymes and cloned into those same sites in the SV3 shuttle vector to generate the intermediate clone Fc-SV3.

The DDD3 and DDD3C inserts were then excised from the pGemT vectors with BspHI and BglII and ligated with Fc-SV3 vector that was digested with NcoI (BspHI compatible ends) and BglII to generate the shuttle vectors DDD3-Fc-SV3 and DDD3C-Fc-SV3, respectively. Finally, the expression cassettes were excised from the SV3 shuttle vectors with XbaI and BamHI and ligated with AD2-pdHL2 vector that was prepared by digestion of h679-AD2-pdHL2 with XbaI and BamHI. The final expression constructs are DDD3-Fc-AD2-pDHL2 and DDD3C-Fc-AD2-pdHL2.

The amino acid sequence of DDD3C-Fc-AD2 is shown in FIG. 6. The amino acid sequence of DDD3-Fc-AD2 is the same except that the 5 amino-terminal residues of DDD3C-Fc-AD2, namely MSCGG, are replaced with MS.

Both expression vectors are transfected into Sp/EEE cells. Positive clones are screened by ELISA using Protein-A coated plates for capture and HRP-conjugated anibody for detection. Purification is accomplished using protein-A affinity chromatography.

Example 9

Treating Focal, Transient Brain Ischemia with an Agent Composed of DDD3C—CH2-CH3-AD2 Linked to Brain-Derived Neurotrophic Factor (BDNF) and a Monoclonal Antibody to Human Transferrin Receptor (hTfR)

Within one hour of onset of the symptoms of a stroke, patient TF is given an i.v. injection of 10 mg of the complex comprising four BDNF-DDD2 modules and one anti-hTfR Fab-AD3 module stably linked to the DDD3C-Fc-AD2 module in saline. The timely intervention reduces the total hemisphere infarct volume as shown by MRI, with the presenting signs and symptoms of partial limb paralysis, speech difficulty, confusion improving markedly within 48 hours while the patient also receives other supportive and anti-coagulant therapy.

TABLE 1

Compositions of selected X$_2$(Ma)Y$_2$ assemblies

| Ma | X | Y | Application |
|---|---|---|---|
| HSP70 | N-A1-B1 | A3-B3 | CEA cancer vaccine |
| | Anti-CD74 Fab | N-A1-B1 | CEA cancer vaccine |
| | Anti-CD74 Fab | A3-B3 | CEA cancer vaccine |
| | Anti-CD205 fab | N-A1-B1 | CEA cancer vaccine |
| | Anti-CD205 Fab | A3-B3 | CEA cancer vaccine |
| | Anti-CD209 Fab | N-A1-B1 | CEA cancer vaccine |
| | Anti-CD209 Fab | A3-B3 | CEA cancer vaccine |
| α$_2$-macroglobulin | N-A1-B1 | A3-B3 | CEA cancer vaccine |
| | Anti-CD74 Fab | N-A1-B1 | CEA cancer vaccine |
| | Anti-CD74 Fab | A3-B3 | CEA cancer vaccine |
| | Anti-CD205 fab | N-A1-B1 | CEA cancer vaccine |
| | Anti-CD205 Fab | A3-B3 | CEA cancer vaccine |
| | Anti-CD209 Fab | N-A1-B1 | CEA cancer vaccine |
| | Anti-CD209 Fab | A3-B3 | CEA cancer vaccine |
| HSA | Anti-hTfR Fab | BDNF | Neuroprotection following strokes |
| | Anti-hTfR Fab | Neuropeptides | Treating CNS disorders |
| Human transferrin (hTf) | G-CSF | Anti-EGFR Fab | Treating solid tumors |
| | Anti-VEGF Fab | Anti-EGFR Fab | Treating solid tumors |

TABLE 2

Compositions of selected X(Mb)$_2$Y assemblies

| (Mb)$_2$ | X | Y | Application |
|---|---|---|---|
| Fc | Anti-CD20 Fab | Anti-CD22 Fab | Cancer therapy |
| | Anti-CD20 Fab | Anti-CD19 Fab | Cancer therapy |
| | Anti-HER2 Fab | Anti-EGFR Fab | Cancer therapy |
| | Anti-IGF-1R Fab | Anti-EGFR Fab | Cancer therapy |
| | Anti-VEGFR1 Fab | Anti-VEGFR2 Fab | Cancer therapy |
| | Anti-VEGFR3 Fab | Anti-VEGFR2 Fab | Cancer therapy |
| | Anti-CD19 Fab | Anti-CD3 Fab | Cancer therapy |
| | Anti-CD19 Fab | Anti-CD64 Fab | Cancer therapy |
| | Anti-HER2 Fab | Anti-CD89 Fab | Cancer therapy |
| | Anti-HER2 Fab | Anti-CD16 Fab | Cancer therapy |
| | Anti-HER2 Fab | Anti-CD64 Fab | Cancer therapy |
| | Anti-HER2 Fab | Anti-CD3 Fab | Cancer therapy |
| | Anti-HER2 Fab | Anti-HER3 Fab | Cancer therapy |
| | Anti-EGFR Fab | Anti-CD2 Fab | Cancer therapy |
| | Anti-EGFR Fab | Anti-CD16 Fab | Cancer therapy |
| | Anti-EGFR Fab | Anti-CD64 Fab | Cancer therapy |
| | Anti-EGFR Fab | Anti-CD89 Fab | Cancer therapy |
| | Anti-MUC1 Fab | Anti-CD64 Fab | Cancer therapy |
| | Anti-CD19 Fab | Anti-CD22 Fab | Cancer therapy |
| | Anti-hTfR Fab | BDNF | Neuroprotection following strokes |
| | Anti-hTfR Fab | Neuropeptides | Treating CNS disorders |
| (hP1)$_2$ | Anti-hTfR Fab | Anti-hIR Fab | Gene therapy for brain cancers |
| | Anti-hTfR Fab | Anti-IGF-1R Fab | Gene therapy for brain cancers |

TABLE 3

Compositions of selected X$_2$(Mc)$_2$ X$_2$ assemblies

| (Mc)$_2$ | X | Application |
|---|---|---|
| Fc | Protamine/DNA-based vaccines | DNA vaccines |
| | Protamine/siRNAs | Therapy |
| | Anti-VEGF Fab | Cancer therapy |
| | Anti-CD20 Fab | Cancer therapy |
| | Anti-CD22 Fab | Cancer therapy |
| | Soluble Tumor Necrosis Factor receptor (sTNFR) | As indicated for Enbrel ® |
| (hP1)$_2$ | Anti-hTfR Fab | Gene therapy for brain disorders |

TABLE 4

Compositions of selected X$_2$(Md)$_2$YX$_2$ assemblies

| (Md)$_2$ | X | Y | Application |
|---|---|---|---|
| Fc | Aβ12-28P | Anti-hTfR Fab | Treating Alzheimer's disease |
| Fc | BDNF | Anti-hTfR Fab | Neuroprotection following stroke |
| (hP1)$_2$ | Anti-hTfR Fab | Anti-IGF-1R Fab | Gene therapy for brain cancers |

What is claimed is:

1. A method of delivering a diagnostic or therapeutic agent comprising:
   a) obtaining a complex comprising,
      (i) an adaptor module selected from the group consisting of HSP70, $\alpha_2$ macroglobulin, HSA (human serum albumin), hP1 (human protamine 1), a heat shock protein, a human protamine and an Fc fragment of a human antibody;
      (ii) a first peptide and a second peptide, each peptide attached to the adaptor module and each peptide consisting of an AD moiety or a DDD moiety, wherein the AD moiety consisting of the peptide sequence from an anchoring domain of an AKAP (A-kinase anchoring protein) and the DDD moiety consisting of the peptide sequence from a dimerization and docking domain of protein kinase A RIα, RIβ, RIIα or RIIβ wherein the AD moiety consisting of peptide sequence selected from the group consisting of AD2 (SEQ ID NO: 2) and AD3 (SEQ ID NO: 5) and the DDD moiety consisting of the peptide sequence selected from the group consisting of DDD2 (SEQ ID NO: 1), DDD3 (SEQ ID NO:3) and DDD3C (SEQ ID NO:4); and
      (iii) at least one diagnostic agent or therapeutic agent attached to the first or second peptide; and
   b) administering the complex to a subject.

2. The method of claim 1, wherein the first peptide consisting of AD2 (SEQ ID NO:2), the second peptide consisting of AD3 (SEQ ID NO:5) and the complex further comprises a first effector attached to DDD2 (SEQ ID NO:1) and a second effector attached to DDD3C (SEQ ID NO:4), wherein two DDD2 (SEQ ID NO:1) form a dimer that binds to AD2 (SEQ ID NO:2) and two DDD3C (SEQ ID NO:4) form another dimer that binds to AD3 (SEQ ID NO:5).

3. The method of claim 1, wherein the first peptide consisting of DDD2 (SEQ ID NO:1), the second peptide consisting of DDD3C (SEQ ID NO:4) and the complex further comprises a first effector attached to AD2 (SEQ ID NO:2) and a second effector attached to AD3 (SEQ ID NO:5), wherein two DDD2 (SEQ ID NO:1) form a dimer that binds to the AD2 (SEQ ID NO:2) and two DDD3C (SEQ ID NO:4) form another dimer that binds to the AD3 (SEQ ID NO:5).

4. The method of claim 1, wherein the first peptide consisting of AD2 (SEQ ID NO:2), the second peptide consisting of DDD3 (SEQ ID NO:3) and the complex further comprises a first effector attached to DDD2 (SEQ ID NO:1), wherein two DDD2 (SEQ ID NO:1) form a dimer that binds to AD2 (SEQ ID NO:2) and two DDD3 (SEQ ID NO:3) form another dimer.

5. The method of claim 1, wherein the first peptide consisting of AD2 (SEQ ID NO:2), the second peptide consisting of DDD3C (SEQ ID NO:4) and the complex further comprises a first effector attached to DDD2 (SEQ ID NO:1) and a second effector attached to AD3 (SEQ ID NO:5), wherein two DDD2 (SEQ ID NO:1) form a dimer that binds to AD2 (SEQ ID NO:2) and two DDD3C (SEQ ID NO:4) form another dimer that binds to AD3 (SEQ ID NO:5).

6. The method of claim 1, wherein one peptide is attached to the N-terminal end of the adaptor module and the other peptide is attached to the C-terminal end of the adaptor module.

7. The method of claim 1, wherein the at least one diagnostic agent or therapeutic agent are selected from the group consisting of an antibody, an antigen-binding antibody fragment thereof and a cytokine and wherein the antibody or antigen-binding antibody fragment thereof has a binding affinity for a tumor-associated antigen.

8. The method of claim 7, wherein the antibody fragment is selected from the group consisting of a Fab, a Fab', a Fv, a scFv and a single domain (DAB) antibody fragments.

9. The method of claim 7, wherein the cytokine is selected from the group consisting of G-CSF, interferon-β1a, interferon-α2b and erythropoietin.

10. The method of claim 7, wherein the at least one therapeutic agents are antibodies or antigen-binding antibody fragments selected from the group consisting of anti-CD74 X anti-CD20, anti-CD74 X anti-CD22, anti-CD22 X anti-CD20, anti-CD20 X anti-HLA-DR, anti-CD19 X anti-CD20, anti-CD20 X anti-CD80, anti-CD2 X anti-CD25, anti-CD8 X anti-CD25, anti-CD2 X anti-CD147, anti-CEACAM5 X anti-CD3, anti-CEACAM6 X anti-CD3, anti-EGFR X anti-CD3, anti-HER2/neu X anti-CD3, anti-CD20 X anti-CD3, anti-CD74 X anti-CD3 and anti-CCD22 X anti-CD3.

11. The method of claim 7, wherein therapeutic agent effector is selected from the group consisting of LL1 (anti-CD74), LL2 (anti-CD22), RFB4 (anti-CD22), A20 (anti-CD20), L243 (anti-HLA class II), CC49 (anti-TAG-72), MN-14 (anti-CEA), MN-15 (anti-CEA), 679 (anti-HSG), 734 (anti-In-DTPA), L19 (anti-ED-B fibronectin), R1 (anti-IGF-1R), PAM4 (anti-MUC1), RS7 (anti-EGP-1), adalimumab, infliximab, omalizumab and palivizumab.

12. The method of claim 7, wherein the antibody or antigen-binding antibody fragment is human, humanized or chimeric.

13. The method of claim 1, wherein the therapeutic agent is selected from the group consisting of a chemotherapeutic agent, a cytokine, a chemokine, an anti-angiogenic agent, an apoptotic agent, a drug, a prodrug, a toxin, an enzyme, boron, a radioisotope, an immunomodulator, an antibiotic and a hormone.

14. The method of claim 13, wherein the therapeutic agent is selected from the group consisting of abrin, amantadine, amoxicillin, amphotericin B, ampicillin, aplidin, azaribine, anastrozole, azacytidine, aztreonam, azithromycin, bacitracin, bactrim, Batrafen, bifonazole, bleomycin, bortezomib, bryostatin-1, busulfan, calicheamycin, camptothecin, 10-hydroxycamptothecin, carbenicillin, caspofungin, carmustine, cefaclor, cefazolin, cephalosporins, cefepime, ceftriaxone, cefotaxime, celecoxib, chlorambucil, chloramphenicol, ciprofloxacin, cisplatin, irinotecan (CPT-11), SN-38, carboplatin, cladribine, cyclophosphamide, cytarabine, dacarbazine, docetaxel, dactinomycin, daunomycin glucuronide, daunorubicin, dexamethasone, diethylstilbestrol, diphtheria toxin, DNase I, doxorubicin, 2-pyrrolinodoxorubicine (2P-DOX), doxycycline, cyano-morpholino doxorubicin, doxorubicin glucuronide, epirubicin glucuronide, ethinyl estradiol, estramustine, estrogen receptor binding agents, etoposide, etoposide glucuronide, etoposide phosphate, erythrocycline, erythromycin, flagyl, farnesyl-protein transferase inhibitors, floxuridine (FUdR), 3′,5′-O-dioleoyl-FudR (FUdR-dO), fludarabine, flutamide, fluorouracil, fluoxymesterone, ganciclovir, gentamycin, gelonin, gemcitabine, hydroxyprogesterone caproate, hydroxyurea, idarubicin, ifosfamide, isoniazid, itraconazole, kanamycin, ketoconazole, L-asparaginase, leucovorin, lomustine, mechlorethamine, medroprogesterone acetate, megestrol acetate, melphalan, mercaptopurine, 6-mercaptopurine, methotrexate, mitoxantrone, mithramycin, mitomycin, mitotane, minocycline, naftifine, nalidixic acid, neomycin, navelbine, nitrosourea, nystatin, ranpirnase, oxacillin, paromomycin, penicillin, pentamidine, piperacillin, tazobactam, phenyl butyrate, prednisone, procarbazine, paclitaxel, pentostatin, pokeweed antiviral protein, *Pseudomonas* exotoxin, *Pseudomonas* endotoxin, raloxifene, rapLR1, ribonuclease, ricin, semustine, rifabutin, rifampin, rimantadine, streptomycin, sulfamethoxazole, sulfasalazine, Staphylococcal enterotoxin-A, streptozocin, tamoxifen, taxanes, taxol, testosterone propionate, tetracycline, thalidomide, thioguanine, thiotepa, teniposide, topotecan, transplatinum, trimethoprim sulfamethoxazole, uracil mustard, valacyclovir, vancomycin, bortezomib, vinblastine, vinorelbine, vincristine, zanamivir and zithromycin.

15. The method of claim 13, wherein the radioisotope is selected from the group consisting of $^{212}$Pb, $^{212}$Bi, $^{213}$Bi, $^{211}$At, $^{223}$Ra, $^{225}$Ac, $^{32}$P, $^{33}$P, $^{47}$Sc, $^{67}$Cu, $^{67}$Ga, $^{89}$Sr, $^{90}$Y, $^{111}$Ag, $^{125}$I, $^{131}$I, $^{142}$Pr, $^{161}$Tb, $^{166}$Ho, $^{166}$Dy, $^{177}$Lu, $^{186}$Re, $^{188}$Re, $^{189}$Re), $^{111}$In, $^{125}$I, $^{67}$Ga, $^{191}$Os, $^{193m}$Pt, $^{195m}$Pt and $^{195m}$Hg.

16. The method of claim 13, wherein the toxin is selected from the group consisting of ricin, abrin, ribonuclease, ranpirnase, rapLR1, DNase I, Staphylococcal enterotoxin-A, pokeweed antiviral protein, gelonin, diphtheria toxin, *Pseudomonas* exotoxin and *Pseudomonas* endotoxin.

17. The method of claim 1, wherein the diagnostic agent is selected from the group consisting of a radioisotope, a dye, a contrast agent, a fluorescent agent, an imaging agent, a chemiluminescent agent, a bioluminescent agent, a liposome and a paramagnetic ion.

18. The method of claim 17, wherein the paramagnetic ion is selected from the group consisting of chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III), erbium (III), lanthanum (III), gold (III), lead (II) and bismuth (III).

19. The method of claim 17, wherein the radioisotope is selected from the group consisting of astatine$^{211}$, carbon$^{14}$, chromium$^{51}$, chlorine$^{36}$, cobalt$^{57}$, cobalt$^{58}$, copper$^{62}$, copper$^{64}$, Eu$^{152}$, fluorine$^{18}$, gallium$^{67}$, gallium$^{68}$, hydrogen$^{3}$, iodine$^{123}$, iodine$^{124}$, iodine$^{125}$, iodine$^{131}$, indium$^{111}$, iron$^{52}$, iron$^{59}$, lutetium$^{177}$, phosphorus$^{32}$, phosphorus$^{33}$, rhenium$^{186}$, rhenium$^{188}$, Sc$^{47}$, selenium$^{75}$, silver$^{111}$, sulphur$^{35}$, technetium$^{94m}$, technetium$^{99m}$, yttrium$^{86}$, yttrium$^{90}$ and zirconium$^{89}$.

20. The method of claim 17, wherein the fluorescent agent is selected from the group consisting of Alexa 350, Alexa 430, AMCA, aminoacridine, BODIPY 630/650, BODIPY 650/665, BODIPY-FL, BODIPY-R6G, BODIPY-TMR, BODIPY-TRX, 5-carboxy-4′,5′-dichloro-2′,7′-dimethoxy fluorescein, 5-carboxy-T, 4′,5′,7′-tetrachlorofluorescein, 5-carboxyfluorescein, 5-carboxyrhodamine, 6-carboxyrhodamine, 6-carboxytetramethyl amino, Cascade Blue, Cy2, Cy3, Cy5,6-FAM, dansyl chloride, Fluorescein, HEX, 6-JOE, NBD (7-nitrobenz-2-oxa-1,3-diazole), Oregon Green 488, Oregon Green 500, Oregon Green 514, Pacific Blue, phthalic acid, terephthalic acid, isophthalic acid, cresyl fast violet, cresyl blue violet, brilliant cresyl blue, para-aminobenzoic acid, erythrosine, phthalocyanines, azomethines, cyanines, xanthines, succinylfluoresceins, rare earth metal cryptates, europium trisbipyridine diamine, a europium cryptate or chelate, diamine, dicyanins, La Jolla blue dye, allopycocyanin, allophycocyanin B, phycocyanin C, phycocyanin R, thiamine, phycoerythrocyanin, phycoerythrin R, REG, Rhodamine Green, rhodamine isothiocyanate, Rhodamine Red, ROX, TAMRA, TET, TRIT (tetramethyl rhodamine isothiol), Tetramethylrhodamine, Edans and Texas Red.

21. The method of claim 17, wherein the chemiluminescent agent is selected from the group consisting of luminol, isoluminol, an aromatic acridinium ester, an imidazole, an acridinium salt and an oxalate ester.

22. The method of claim 1 wherein the subject has cancer.

23. The method of claim 22, further comprising administering one or more anti-cancer therapies in combination with the complex.

24. The method of claim 23, wherein the therapy comprises administering a chemotherapeutic agent, a cytokine, radiation therapy, immunotherapy, radioimmunotherapy, localized hyperthermia, laser irradiation, an anti-angiogenic agent or surgical excision.

25. The method of claim 22, wherein the cancer is acute lymphocytic leukemia, acute myelogenous leukemia, renal cell carcinoma, biliary cancer, brain cancers, breast cancer, cervical cancer, chronic lymphocytic leukemia, chronic myelogenous leukemia, multiple myeloma, colorectal cancer, endometrial cancer, esophageal cancer, gastric cancer, head and neck cancer, Hodgkin's lymphoma, lung cancer, medullary thyroid cancer, non-Hodgkin's lymphoma, ovarian cancer, testicular cancer, pancreatic cancer, glioma and other brain and spinal cord tumors, sarcomas, liver cancer, prostate cancer, melanoma or urinary bladder cancer.

* * * * *

SEQUENCE LISTING

```
<160> NUMBER OF SEQ ID NOS: 18

<210> SEQ ID NO 1
<211> LENGTH: 45
<212> TYPE: PRT
<213> ORGANISM: Artificial
<220> FEATURE:
<223> OTHER INFORMATION: synthetic peptide

<400> SEQUENCE: 1

Cys Gly His Ile Gln Ile Pro Pro Gly Leu Thr Glu Leu Leu Gln Gly
1               5                   10                  15
```

```
Tyr Thr Val Glu Val Leu Arg Gln Gln Pro Pro Asp Leu Val Glu Phe
            20                  25                  30

Ala Val Glu Tyr Phe Thr Arg Leu Arg Glu Ala Arg Ala
        35                  40                  45

<210> SEQ ID NO 2
<211> LENGTH: 21
<212> TYPE: PRT
<213> ORGANISM: Artificial
<220> FEATURE:
<223> OTHER INFORMATION: synthetic peptide

<400> SEQUENCE: 2

Cys Gly Gln Ile Glu Tyr Leu Ala Lys Gln Ile Val Asp Asn Ala Ile
1               5                   10                  15

Gln Gln Ala Gly Cys
            20

<210> SEQ ID NO 3
<211> LENGTH: 50
<212> TYPE: PRT
<213> ORGANISM: Artificial
<220> FEATURE:
<223> OTHER INFORMATION: synthetic peptide

<400> SEQUENCE: 3

Ser Leu Arg Glu Cys Glu Leu Tyr Val Gln Lys His Asn Ile Gln Ala
1               5                   10                  15

Leu Leu Lys Asp Ser Ile Val Gln Leu Cys Thr Ala Arg Pro Glu Arg
            20                  25                  30

Pro Met Ala Phe Leu Arg Glu Tyr Phe Glu Arg Leu Glu Lys Glu Glu
        35                  40                  45

Ala Lys
    50

<210> SEQ ID NO 4
<211> LENGTH: 55
<212> TYPE: PRT
<213> ORGANISM: Artificial
<220> FEATURE:
<223> OTHER INFORMATION: synthetic peptide

<400> SEQUENCE: 4

Met Ser Cys Gly Gly Ser Leu Arg Glu Cys Glu Leu Tyr Val Gln Lys
1               5                   10                  15

His Asn Ile Gln Ala Leu Leu Lys Asp Ser Ile Val Gln Leu Cys Thr
            20                  25                  30

Ala Arg Pro Glu Arg Pro Met Ala Phe Leu Arg Glu Tyr Phe Glu Arg
        35                  40                  45

Leu Glu Lys Glu Glu Ala Lys
    50                  55

<210> SEQ ID NO 5
<211> LENGTH: 23
<212> TYPE: PRT
<213> ORGANISM: Artificial
<220> FEATURE:
<223> OTHER INFORMATION: synthetic peptide

<400> SEQUENCE: 5

Cys Gly Phe Glu Glu Leu Ala Trp Lys Ile Ala Lys Met Ile Trp Ser
1               5                   10                  15
```

```
Asp Val Phe Gln Gln Gly Cys
            20
```

```
<210> SEQ ID NO 6
<211> LENGTH: 4
<212> TYPE: PRT
<213> ORGANISM: Artificial
<220> FEATURE:
<223> OTHER INFORMATION: synthetic peptide

<400> SEQUENCE: 6

Gly Arg Ser Gly
1
```

```
<210> SEQ ID NO 7
<211> LENGTH: 110
<212> TYPE: PRT
<213> ORGANISM: Artificial
<220> FEATURE:
<223> OTHER INFORMATION: synthetic peptide

<400> SEQUENCE: 7

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110
```

```
<210> SEQ ID NO 8
<211> LENGTH: 107
<212> TYPE: PRT
<213> ORGANISM: Artificial
<220> FEATURE:
<223> OTHER INFORMATION: synthetic peptide

<400> SEQUENCE: 8

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105
```

```
<210> SEQ ID NO 9
```

```
<211> LENGTH: 9
<212> TYPE: PRT
<213> ORGANISM: Artificial
<220> FEATURE:
<223> OTHER INFORMATION: synthetic peptide

<400> SEQUENCE: 9

Gly Ser Gly Gly Gly Gly Ser Gly Gly
1               5

<210> SEQ ID NO 10
<211> LENGTH: 14
<212> TYPE: PRT
<213> ORGANISM: Artificial
<220> FEATURE:
<223> OTHER INFORMATION: synthetic peptide

<400> SEQUENCE: 10

Arg Arg Arg Arg Arg Arg Gly Gly Arg Arg Arg Arg Arg Arg
1               5                   10

<210> SEQ ID NO 11
<211> LENGTH: 27
<212> TYPE: DNA
<213> ORGANISM: Artificial
<220> FEATURE:
<223> OTHER INFORMATION: synthetic oligonucleotide

<400> SEQUENCE: 11
agatctgcct tttgcctcct ccttctc                                    27

<210> SEQ ID NO 12
<211> LENGTH: 26
<212> TYPE: DNA
<213> ORGANISM: Artificial
<220> FEATURE:
<223> OTHER INFORMATION: synthetic oligonucleotide

<400> SEQUENCE: 12
tcatgagcct tcgagaatgt gagctc                                     26

<210> SEQ ID NO 13
<211> LENGTH: 36
<212> TYPE: DNA
<213> ORGANISM: Artificial
<220> FEATURE:
<223> OTHER INFORMATION: synthetic oligonucleotide

<400> SEQUENCE: 13
tcatgagttg tggcggaagc cttcgagaat gtgagc                          36

<210> SEQ ID NO 14
<211> LENGTH: 24
<212> TYPE: DNA
<213> ORGANISM: Artificial
<220> FEATURE:
<223> OTHER INFORMATION: synthetic oligonucleotide

<400> SEQUENCE: 14
agatctggcg cacctgaact cctg                                       24

<210> SEQ ID NO 15
<211> LENGTH: 33
<212> TYPE: DNA
<213> ORGANISM: Artificial
<220> FEATURE:
<223> OTHER INFORMATION: synthetic oligonucleotide
```

```
<400> SEQUENCE: 15
gaattcggat cctttacccg gagacaggga gag                              33

<210> SEQ ID NO 16
<211> LENGTH: 19
<212> TYPE: PRT
<213> ORGANISM: Artificial
<220> FEATURE:
<223> OTHER INFORMATION: synthetic peptide

<400> SEQUENCE: 16

Ser His Arg Tyr Arg Leu Ala Ile Gln Leu His Ala Ser Asp Ser Ser
1               5                   10                  15

Ser Cys Val

<210> SEQ ID NO 17
<211> LENGTH: 9
<212> TYPE: PRT
<213> ORGANISM: Artificial
<220> FEATURE:
<223> OTHER INFORMATION: synthetic peptide

<400> SEQUENCE: 17

Gln Asp Asp His Leu Thr Thr Gly Arg
1               5

<210> SEQ ID NO 18
<211> LENGTH: 12
<212> TYPE: PRT
<213> ORGANISM: Artificial
<220> FEATURE:
<223> OTHER INFORMATION: synthetic peptide

<400> SEQUENCE: 18

Arg Met Pro Tyr Ser Glu His Ser Ala Pro Leu Gly
1               5                   10
```